(12) United States Patent
Fung

(10) Patent No.: US 7,294,481 B1
(45) Date of Patent: Nov. 13, 2007

(54) METHOD FOR PRODUCING RECOMBINANT PROTEINS

(75) Inventor: Victor P. Fung, Redmond, WA (US)

(73) Assignee: Immunex Corporation

( * ) Notice: Subject to any disclaimer, the term of this patent is extended or adjusted under 35 U.S.C. 154(b) by 630 days.

(21) Appl. No.: 10/233,250

(22) Filed: Aug. 30, 2002

Related U.S. Application Data

(63) Continuation of application No. 09/225,358, filed on Jan. 5, 1999, now abandoned.

(51) Int. Cl.
*C12N 15/00* (2006.01)
*C12P 21/00* (2006.01)

(52) U.S. Cl. .................. 435/69.1; 435/70.1; 435/235.1; 435/325; 435/335; 435/383; 435/384; 435/320.1; 435/69.7; 436/547; 530/351; 530/387.1

(58) Field of Classification Search ...................... None
See application file for complete search history.

(56) References Cited

U.S. PATENT DOCUMENTS

| | | | |
|---|---|---|---|
| 4,216,203 A | 8/1980 | Johnston | |
| 4,357,422 A | 11/1982 | Giard | |
| 5,196,523 A | 3/1993 | Lee | |
| 5,395,760 A | 3/1995 | Smith et al. | |
| 5,705,364 A | 1/1998 | Etcheverry | |
| 5,721,121 A | 2/1998 | Etcheverry | |
| 5,976,833 A | 11/1999 | Furukawa et al. | |
| 6,716,602 B2 | 4/2004 | Andersen et al. | |

OTHER PUBLICATIONS

Mather et al, *Large Scale Mammalian Cell Culture Technology*, Marcel Dekker, Inc., New York and Basel, pp. 161-177, (1990).
Takagi et al, *Appl. Microbiol. Biotechnol.*, 41:565-570 (1994).
Bloemkolk et al, *Biotechn. and Bioeng.*, 40:427-431 (1992).
Sureshkumar et al, *Biotechn. and Bioeng.*, 37:292-295 (1991).
Reuveny et al, *J. of Immunol. Methods*, 86:53-59 (1986).
Kamech et al, *Experimental Cell Research*, 162:326-334 (1986).
Oh et al, *Biotechn. And Bioeng.*, 42:601-610 (1993).
Chotigeat et al, *Cytotechnology*, 15:217-221 (1994).
Palermo et al, *J. of Biotech.*, 19:35-48 (1991).
Weidemann et al, *Cytotechnology*, 15:111-116 (1994).
Moore et al, *Cytotechnology*, 23:47-54 (1997).
Guppy et al, *Vox Sang*, 62:70-75 (1992).
Tsao et al, *Biotechn. And Bioeng.*, 40:1190-1196 (1992).
Morris et al, *Animal Cell Technology*, pp. 529-534 (1997).
Kaptein et al, *Gene Ther.*, 4(2):172-176 (1997)—Abstract.
Jordan et al, *Nucleic Acids Res.*, 24(4):596-601 (1996)—Abstract.
Kirinaka et al, *Appl. Microbiol. Biotechnol.*, 41(5):591-591 (1994)—Abstract.
Yu et al, *Archives of Dermatological Res.*, 289(6):352-359 (1997)—Abstract.

*Primary Examiner*—Gary B. Nickol
*Assistant Examiner*—Nirmal S. Basi
(74) *Attorney, Agent, or Firm*—Sughrue Mion Pllc.

(57) ABSTRACT

A method for producing recombinant proteins, preferably fusion proteins comprising an Fc portion of an immunoglobulin molecule, more preferably fusion proteins comprising an extracellular domain of a tumor necrosis factor receptor fused to the Fc portion of an immunoglobulin molecule, is disclosed. The method of the present invention allows a reduction of misfolding of the protein, thereby giving rise to a higher yield of the desired protein.

33 Claims, 5 Drawing Sheets

SEQUENCE LISTING

<160> NUMBER OF SEQ ID NOS: 12

<210> SEQ ID NO 1
<211> LENGTH: 51
<212> TYPE: DNA
<213> ORGANISM: Synthetic Construct

<400> SEQUENCE: 1
ccccagctga agggagcact ggcgacgagc ccaaatcttg tgacaaaact c         51

<210> SEQ ID NO 2
<211> LENGTH: 22
<212> TYPE: DNA
<213> ORGANISM: Synthetic Construct

<400> SEQUENCE: 2
cggtacgtgc tgttgttact gc                                          22

<210> SEQ ID NO 3
<211> LENGTH: 1557
<212> TYPE: DNA
<213> ORGANISM: Synthetic Construct

<400> SEQUENCE: 3

```
gcgaggcagg cagcctggag agaaggcgct gggctgcgag ggcgcgaggg cgcgagggca      60
ggggcaacc ggaccccgcc cgcatccatg gcgcccgtcg ccgtctgggc cgcgctggcc     120
gtcggactgg agctctgggc tgcggcgcac gccttgcccg cccaggtggc atttacaccc     180
tacgccccgg agcccgggag cacatgccgg ctcagagaat actatgacca gacagctcag     240
atgtgctgca gcaaatgctc gccgggccaa catgcaaaag tcttctgtac caagacctcg     300
gacaccgtgt gtgactcctg tgaggacagc acatacaccc agctctggaa ctgggttccc     360
gagtgcttga gctgtggctc ccgctgtagc tctgaccagg tggaaactca agcctgcact     420
cgggaacaga accgcatctg cacctgcagg cccggctggt actgcgcgct gagcaagcag     480
gaggggtgcc ggctgtgcgc gccgctgcgc aagtgccgcc cgggcttcgg cgtggccaga     540
ccaggaactg aaacatcaga cgtggtgtgc aagccctgtg ccccggggac gttctccaac     600
acgacttcat ccacggatat ttgcaggccc accagatct gtaacgtggt ggccatccct     660
gggaatgcaa gcatggatgc agtctgcacg tccacgtccc ccaccggag tatggcccca     720
ggggcagtac acttacccca gccagtgtcc acacgatccc aacacacgca gccaactcca     780
gaacccagca ctgctccaag cacctccttc ctgctcccaa tgggccccag ccccccagct     840
gaagggagca ctggcgacga gcccaaatct tgtgacaaaa ctcacacatg cccaccgtgc     900
ccagcacctg aactcctggg gggaccgtca gtcttcctct tccccccaaa acccaaggac     960
accctcatga tctcccggac ccctgaggtc acatgcgtgg tggtggacgt gagccacgaa    1020
gaccctgagg tcaggttcaa ctggtacgtg gacggcgtgg aggtgcataa tgccaagaca    1080
aagccgcggg aggagcagta caacagcacg taccgggtgg tcagcgtcct caccgtcctg    1140
caccaggact ggctgaatgg caaggactac aagtgcaagg tctccaacaa agccctccca    1200
gcccccatgc agaaaaccat ctccaaagcc aaagggcagc cccgagaacc acaggtgtac    1260
accctgcccc catcccggga tgagctgacc aagaaccagg tcagcctgac ctgcctggtc    1320
aaaggcttct atcccaggca catcgccgtg gagtgggaga gcaatgggca gccggagaac    1380
aactacaaga ccacgcctcc cgtgctggac tccgacggct ccttcttcct ctacagcaag    1440
ctcaccgtgg acaagagcag gtggcagcag gggaacgtct tctcatgctc cgtgatgcat    1500
gaggctctgc acaaccacta cacgcagaag agcctctccc tgtctccggg taaatga       1557
```

<210> SEQ ID NO 4
<211> LENGTH: 518
<212> TYPE: PRT
<213> ORGANISM: Synthetic Construct

<400> SEQUENCE: 4

```
Ala Arg Gln Ala Ala Trp Arg Glu Gly Ala Gly Leu Arg Gly Arg Glu
1               5                   10                  15
Gly Ala Arg Ala Gly Gly Asn Arg Thr Pro Pro Ala Ser Met Ala Pro
            20                  25                  30
Val Ala Val Trp Ala Ala Leu Ala Val Gly Leu Glu Leu Trp Ala Ala
        35                  40                  45
Ala His Ala Leu Pro Ala Gln Val Ala Phe Thr Pro Tyr Ala Pro Glu
    50                  55                  60
Pro Gly Ser Thr Cys Arg Leu Arg Glu Tyr Tyr Asp Gln Thr Ala Gln
65                  70                  75                  80
Met Cys Cys Ser Lys Cys Ser Pro Gly Gln His Ala Lys Val Phe Cys
                85                  90                  95
```

-continued

```
Thr Lys Thr Ser Asp Thr Val Cys Asp Ser Cys Glu Asp Ser Thr Tyr
            100                 105                 110

Thr Gln Leu Trp Asn Trp Val Pro Glu Cys Leu Ser Cys Gly Ser Arg
            115                 120                 125

Cys Ser Ser Asp Gln Val Glu Thr Gln Ala Cys Thr Arg Glu Gln Asn
            130                 135                 140

Arg Ile Cys Thr Cys Arg Pro Gly Trp Tyr Cys Ala Leu Ser Lys Gln
145                 150                 155                 160

Glu Gly Cys Arg Leu Cys Ala Pro Leu Arg Lys Cys Arg Pro Gly Phe
                165                 170                 175

Gly Val Ala Arg Pro Gly Thr Glu Thr Ser Asp Val Val Cys Lys Pro
            180                 185                 190

Cys Ala Pro Gly Thr Phe Ser Asn Thr Thr Ser Ser Thr Asp Ile Cys
            195                 200                 205

Arg Pro His Gln Ile Cys Asn Val Val Ala Ile Pro Gly Asn Ala Ser
            210                 215                 220

Met Asp Ala Val Cys Thr Ser Thr Ser Pro Thr Arg Ser Met Ala Pro
225                 230                 235                 240

Gly Ala Val His Leu Pro Gln Pro Val Ser Thr Arg Ser Gln His Thr
                245                 250                 255

Gln Pro Thr Pro Glu Pro Ser Thr Ala Pro Ser Thr Ser Phe Leu Leu
            260                 265                 270

Pro Met Gly Pro Ser Pro Pro Ala Glu Gly Ser Thr Gly Asp Glu Pro
            275                 280                 285

Lys Ser Cys Asp Lys Thr His Thr Cys Pro Pro Cys Pro Ala Pro Glu
            290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
            340                 345                 350

Val Glu Val His Asn Ala Lys Thr Lys Pro Arg Glu Glu Gln Tyr Asn
            355                 360                 365

Ser Thr Tyr Arg Val Val Ser Val Leu Thr Val Leu His Gln Asp Trp
            370                 375                 380

Leu Asn Gly Lys Asp Tyr Lys Cys Lys Val Ser Asn Lys Ala Leu Pro
385                 390                 395                 400

Ala Pro Met Gln Lys Thr Ile Ser Lys Ala Lys Gly Gln Pro Arg Glu
                405                 410                 415

Pro Gln Val Tyr Thr Leu Pro Pro Ser Arg Asp Glu Leu Thr Lys Asn
            420                 425                 430

Gln Val Ser Leu Thr Cys Leu Val Lys Gly Phe Tyr Pro Arg His Ile
            435                 440                 445

Ala Val Glu Trp Glu Ser Asn Gly Gln Pro Glu Asn Asn Tyr Lys Thr
            450                 455                 460

Thr Pro Pro Val Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
            500                 505                 510
```

Ser Leu Ser Pro Gly Lys
    515

<210> SEQ ID NO 5
<211> LENGTH: 36
<212> TYPE: DNA
<213> ORGANISM: Synthetic Construct

<400> SEQUENCE: 5
atcacacacg gtgtccgagg tcttggtaca gaagac                              36

<210> SEQ ID NO 6
<211> LENGTH: 40
<212> TYPE: DNA
<213> ORGANISM: Synthetic Construct

<400> SEQUENCE: 6
atctaggatc cgccgccacc atggcgcccg tcgccgtctg                          40

<210> SEQ ID NO 7
<211> LENGTH: 67
<212> TYPE: DNA
<213> ORGANISM: Synthetic Construct

<400> SEQUENCE: 7
ccggtttaaa cgtcgacatc ccgggatcct aggatccgga tcgatcggac cgcggccgcg    60
tttaaac                                                              67

<210> SEQ ID NO 8
<211> LENGTH: 67
<212> TYPE: DNA
<213> ORGANISM: Synthetic Construct

<400> SEQUENCE: 8
ggccgtttaa acgcggccgc ggtccgatcg atccggatcc taggatcccg ggatgtcgac    60
gtttaaa                                                              67

<210> SEQ ID NO 9
<211> LENGTH: 2051
<212> TYPE: DNA
<213> ORGANISM: Human
<220> FEATURE:
<221> NAME/KEY: CDS
<222> LOCATION: (187)..(1491)
<220> FEATURE:
<221> NAME/KEY: mat_peptide
<222> LOCATION: (274)..()

<400> SEQUENCE: 9
gaattcgggg gggttcaaga tcactgggac caggccgtga tctctatgcc cgagtctcaa    60
ccctcaactg tcaccccaag gcacttggga cgtcctggac agaccgagtc ccgggaagcc   120
ccagcactgc cgctgccaca ctgccctgag cccaaatggg ggagtgagag gccatagctg   180 tctggc atg ggc ctc tcc acc gtg cct gac ctg ctg ctg ccg ctg gtg     228
       Met Gly Leu Ser Thr Val Pro Asp Leu Leu Leu Pro Leu Val
           -25                 -20 ctc ctg gag ctg ttg gtg gga ata tac ccc tca ggg gtt att gga ctg     276
Leu Leu Glu Leu Leu Val Gly Ile Tyr Pro Ser Gly Val Ile Gly Leu
-15                 -10                 -5              -1  1 gtc cct cac cta ggg gac agg gag aag aga gat agt gtg tgt ccc caa     324
Val Pro His Leu Gly Asp Arg Glu Lys Arg Asp Ser Val Cys Pro Gln
                5                  10                  15

-continued

```
gga aaa tat atc cac cct caa aat aat tcg att tgc acg gac tgc agg        372
Gly Lys Tyr Ile His Pro Gln Asn Asn Ser Ile Cys Thr Asp Cys Arg
         20              25                  30 gag tgt gag agc ggc tcc ttc acc gct tca gaa aac cac ctc aga cac        420
Glu Cys Glu Ser Gly Ser Phe Thr Ala Ser Glu Asn His Leu Arg His
 35              40                  45 tgc ctc agc tgc tcc aaa tgc cga aag gaa atg ggt cag gtg gag atc        468
Cys Leu Ser Cys Ser Lys Cys Arg Lys Glu Met Gly Gln Val Glu Ile
 50              55                  60                  65 tct tct tgc aca gtg gac cgg gac acc gtg tgt ggc tgc agg aag aac        516
Ser Ser Cys Thr Val Asp Arg Asp Thr Val Cys Gly Cys Arg Lys Asn
                 70                  75                  80 cag tac cgg cat tat tgg agt gaa aac ctt ttc cag tgc ttc aat tgc        564
Gln Tyr Arg His Tyr Trp Ser Glu Asn Leu Phe Gln Cys Phe Asn Cys
             85                  90                  95 agc ctc tgc ctc aat ggg acc gtg cac ctc tcc tgc cag gag aaa cag        612
Ser Leu Cys Leu Asn Gly Thr Val His Leu Ser Cys Gln Glu Lys Gln
        100                 105                 110 aac acc gtg tgc acc tgc cat gca ggt ttc ttt cta aga gaa aac gag        660
Asn Thr Val Cys Thr Cys His Ala Gly Phe Phe Leu Arg Glu Asn Glu
        115                 120                 125 tgt gtc tcc tgt agt aac tgt aag aaa agc ctg gag tgc acg aag ttg        708
Cys Val Ser Cys Ser Asn Cys Lys Lys Ser Leu Glu Cys Thr Lys Leu
130                 135                 140                 145 tgc cta ccc cag att gag aat gtt aag ggc act gag gac tca ggc acc        756
Cys Leu Pro Gln Ile Glu Asn Val Lys Gly Thr Glu Asp Ser Gly Thr
                150                 155                 160 aca gtg ctg ttg ccc ctg gtc att ttc ttt ggt ctt tgc ctt tta tcc        804
Thr Val Leu Leu Pro Leu Val Ile Phe Phe Gly Leu Cys Leu Leu Ser
            165                 170                 175 ctc ctc ttc att ggt tta atg tat cgc tac caa cgg tgg aag tcc aag        852
Leu Leu Phe Ile Gly Leu Met Tyr Arg Tyr Gln Arg Trp Lys Ser Lys
        180                 185                 190 ctc tac tcc att gtt tgt ggg aaa tcg aca cct gaa aaa gag ggg gag        900
Leu Tyr Ser Ile Val Cys Gly Lys Ser Thr Pro Glu Lys Glu Gly Glu
        195                 200                 205 ctt gaa gga act act act aag ccc ctg gcc cca aac cca agc ttc agt        948
Leu Glu Gly Thr Thr Thr Lys Pro Leu Ala Pro Asn Pro Ser Phe Ser
210                 215                 220                 225 ccc act cca ggc ttc acc ccc acc ctg ggc ttc agt ccc gtg ccc agt        996
Pro Thr Pro Gly Phe Thr Pro Thr Leu Gly Phe Ser Pro Val Pro Ser
                230                 235                 240 tcc acc ttc acc tcc agc tcc acc tat acc ccc ggt gac tgt ccc aac       1044
Ser Thr Phe Thr Ser Ser Ser Thr Tyr Thr Pro Gly Asp Cys Pro Asn
            245                 250                 255 ttt gcg gct ccc cgc aga gag gtg gca cca ccc tat cag ggg gct gac       1092
Phe Ala Ala Pro Arg Arg Glu Val Ala Pro Pro Tyr Gln Gly Ala Asp
        260                 265                 270 ccc atc ctt gcg aca gcc ctc gcc tcc gac ccc atc ccc aac ccc ctt       1140
Pro Ile Leu Ala Thr Ala Leu Ala Ser Asp Pro Ile Pro Asn Pro Leu
        275                 280                 285 cag aag tgg gag gac agc gcc cac aag cca cag agc cta gac act gat       1188
Gln Lys Trp Glu Asp Ser Ala His Lys Pro Gln Ser Leu Asp Thr Asp
290                 295                 300                 305 gac ccc gcg acg ctg tac gcc gtg gtg gag aac gtg ccc ccg ttg cgc       1236
Asp Pro Ala Thr Leu Tyr Ala Val Val Glu Asn Val Pro Pro Leu Arg
                310                 315                 320 tgg aag gaa ttc gtg cgg cgc cta ggg ctg agc gac cac gag atc gat       1284
Trp Lys Glu Phe Val Arg Arg Leu Gly Leu Ser Asp His Glu Ile Asp
            325                 330                 335
```

-continued

```
cgg ctg gag ctg cag aac ggg cgc tgc ctg cgc gag gcg caa tac agc      1332
Arg Leu Glu Leu Gln Asn Gly Arg Cys Leu Arg Glu Ala Gln Tyr Ser
        340                 345                 350 atg ctg gcg acc tgg agg cgg cgc acg ccg cgg cgc gag gcc acg ctg      1380
Met Leu Ala Thr Trp Arg Arg Arg Thr Pro Arg Arg Glu Ala Thr Leu
    355                 360                 365 gag ctg ctg gga cgc gtg ctc cgc gac atg gac ctg ctg ggc tgc ctg      1428
Glu Leu Leu Gly Arg Val Leu Arg Asp Met Asp Leu Leu Gly Cys Leu
370                 375                 380                 385 gag gac atc gag gag gcg ctt tgc ggc ccc gcc gcc ctc ccg ccc gcg      1476
Glu Asp Ile Glu Glu Ala Leu Cys Gly Pro Ala Ala Leu Pro Pro Ala
                390                 395                 400 ccc agt ctt ctc aga tgaggctgcg ccctgcggg cagtctaag gaccgtcctg        1531
Pro Ser Leu Leu Arg
            405 cgagatcgcc ttccaacccc acttttttct ggaaaggagg ggtcctgcag gggcaagcag   1591 gagctagcag ccgcctactt ggtgctaacc cctcgatgta catagctttt ctcagctgcc   1651 tgcgcgccgc cgacagtcag cgctgtgcgc gcggagagag gtgcgccgtg ggctcaagag   1711 cctgagtggg tggtttgcga ggatgaggga cgctatgcct catgcccgtt ttgggtgtcc   1771 tcaccagcaa ggctgctcgg gggcccctgg ttcgtccctg agccttttc acagtgcata    1831 agcagttttt tttgtttttg ttttgttttg ttttgttttt aaatcaatca tgttacacta   1891 atagaaactt ggcactcctg tgccctctgc ctggacaagc acatagcaag ctgaactgtc   1951 ctaaggcagg ggcgagcacg gaacaatggg gccttcagct ggagctgtgg acttttgtac   2011 atacactaaa attctgaagt taaaaaaaaa acccgaattc                         2051
```

<210> SEQ ID NO 10
<211> LENGTH: 435
<212> TYPE: PRT
<213> ORGANISM: Human

<400> SEQUENCE: 10

```
Met Gly Leu Ser Thr Val Pro Asp Leu Leu Pro Leu Val Leu Leu
            -25                 -20                 -15

Glu Leu Leu Val Gly Ile Tyr Pro Ser Gly Val Ile Gly Leu Val Pro
        -10                  -5                  -1   1

His Leu Gly Asp Arg Glu Lys Arg Asp Ser Val Cys Pro Gln Gly Lys
        5                   10                  15

Tyr Ile His Pro Gln Asn Asn Ser Ile Cys Thr Asp Cys Arg Glu Cys
20                  25                  30                  35

Glu Ser Gly Ser Phe Thr Ala Ser Glu Asn His Leu Arg His Cys Leu
                40                  45                  50

Ser Cys Ser Lys Cys Arg Lys Glu Met Gly Gln Val Glu Ile Ser Ser
            55                  60                  65

Cys Thr Val Asp Arg Asp Thr Val Cys Gly Cys Arg Lys Asn Gln Tyr
        70                  75                  80

Arg His Tyr Trp Ser Glu Asn Leu Phe Gln Cys Phe Asn Cys Ser Leu
    85                  90                  95

Cys Leu Asn Gly Thr Val His Leu Ser Cys Gln Glu Lys Gln Asn Thr
100                 105                 110                 115

Val Cys Thr Cys His Ala Gly Phe Phe Leu Arg Glu Asn Glu Cys Val
                120                 125                 130

Ser Cys Ser Asn Cys Lys Lys Ser Leu Glu Cys Thr Lys Leu Cys Leu
            135                 140                 145
```

-continued

```
Pro Gln Ile Glu Asn Val Lys Gly Thr Glu Asp Ser Gly Thr Thr Val
        150                 155                 160

Leu Leu Pro Leu Val Ile Phe Phe Gly Leu Cys Leu Leu Ser Leu Leu
    165                 170                 175

Phe Ile Gly Leu Met Tyr Arg Tyr Gln Arg Trp Lys Ser Lys Leu Tyr
180                 185                 190                 195

Ser Ile Val Cys Gly Lys Ser Thr Pro Glu Lys Glu Gly Glu Leu Glu
                200                 205                 210

Gly Thr Thr Thr Lys Pro Leu Ala Pro Asn Pro Ser Phe Ser Pro Thr
            215                 220                 225

Pro Gly Phe Thr Pro Thr Leu Gly Phe Ser Pro Val Pro Ser Ser Thr
        230                 235                 240

Phe Thr Ser Ser Ser Thr Tyr Thr Pro Gly Asp Cys Pro Asn Phe Ala
    245                 250                 255

Ala Pro Arg Arg Glu Val Ala Pro Pro Tyr Gln Gly Ala Asp Pro Ile
260                 265                 270                 275

Leu Ala Thr Ala Leu Ala Ser Asp Pro Ile Pro Asn Pro Leu Gln Lys
                280                 285                 290

Trp Glu Asp Ser Ala His Lys Pro Gln Ser Leu Asp Thr Asp Asp Pro
            295                 300                 305

Ala Thr Leu Tyr Ala Val Val Glu Asn Val Pro Pro Leu Arg Trp Lys
        310                 315                 320

Glu Phe Val Arg Arg Leu Gly Leu Ser Asp His Glu Ile Asp Arg Leu
    325                 330                 335

Glu Leu Gln Asn Gly Arg Cys Leu Arg Glu Ala Gln Tyr Ser Met Leu
340                 345                 350                 355

Ala Thr Trp Arg Arg Arg Thr Pro Arg Arg Glu Ala Thr Leu Glu Leu
                360                 365                 370

Leu Gly Arg Val Leu Arg Asp Met Asp Leu Leu Gly Cys Leu Glu Asp
            375                 380                 385

Ile Glu Glu Ala Leu Cys Gly Pro Ala Ala Leu Pro Pro Ala Pro Ser
        390                 395                 400

Leu Leu Arg
    405

<210> SEQ ID NO 11
<211> LENGTH: 1641
<212> TYPE: DNA
<213> ORGANISM: Human
<220> FEATURE:
<221> NAME/KEY: CDS
<222> LOCATION: (88)..(1470)
<220> FEATURE:
<221> NAME/KEY: mat_peptide
<222> LOCATION: (154)..()

<400> SEQUENCE: 11
gcgaggcagg cagcctggag agaaggcgct gggctgcgag ggcgcgaggg cgcgagggca         60
gggggcaacc ggaccccgcc cgcatcc atg gcg ccc gtc gcc gtc tgg gcc gcg       114
                                Met Ala Pro Val Ala Val Trp Ala Ala
                                    -20                 -15 ctg gcc gtc gga ctg gag ctc tgg gct gcg gcg cac gcc ttg ccc gcc        162
Leu Ala Val Gly Leu Glu Leu Trp Ala Ala Ala His Ala Leu Pro Ala
        -10                 -5             -1 1 cag gtg gca ttt aca ccc tac gcc ccg gag ccc ggg agc aca tgc cgg        210
Gln Val Ala Phe Thr Pro Tyr Ala Pro Glu Pro Gly Ser Thr Cys Arg
     5                  10                  15
```

-continued

```
ctc aga gaa tac tat gac cag aca gct cag atg tgc tgc agc aaa tgc      258
Leu Arg Glu Tyr Tyr Asp Gln Thr Ala Gln Met Cys Cys Ser Lys Cys
 20              25                  30                  35 tcg ccg ggc caa cat gca aaa gtc ttc tgt acc aag acc tcg gac acc      306
Ser Pro Gly Gln His Ala Lys Val Phe Cys Thr Lys Thr Ser Asp Thr
                 40                  45                  50 gtg tgt gac tcc tgt gag gac agc aca tac acc cag ctc tgg aac tgg      354
Val Cys Asp Ser Cys Glu Asp Ser Thr Tyr Thr Gln Leu Trp Asn Trp
             55                  60                  65 gtt ccc gag tgc ttg agc tgt ggc tcc cgc tgt agc tct gac cag gtg      402
Val Pro Glu Cys Leu Ser Cys Gly Ser Arg Cys Ser Ser Asp Gln Val
         70                  75                  80 gaa act caa gcc tgc act cgg gaa cag aac cgc atc tgc acc tgc agg      450
Glu Thr Gln Ala Cys Thr Arg Glu Gln Asn Arg Ile Cys Thr Cys Arg
     85                  90                  95 ccc ggc tgg tac tgc gcg ctg agc aag cag gag ggg tgc cgg ctg tgc      498
Pro Gly Trp Tyr Cys Ala Leu Ser Lys Gln Glu Gly Cys Arg Leu Cys
100                 105                 110                 115 gcg ccg ctg cgc aag tgc cgc ccg ggc ttc ggc gtg gcc aga cca gga      546
Ala Pro Leu Arg Lys Cys Arg Pro Gly Phe Gly Val Ala Arg Pro Gly
                120                 125                 130 act gaa aca tca gac gtg gtg tgc aag ccc tgt gcc ccg ggg acg ttc      594
Thr Glu Thr Ser Asp Val Val Cys Lys Pro Cys Ala Pro Gly Thr Phe
            135                 140                 145 tcc aac acg act tca tcc acg gat att tgc agg ccc cac cag atc tgt      642
Ser Asn Thr Thr Ser Ser Thr Asp Ile Cys Arg Pro His Gln Ile Cys
        150                 155                 160 aac gtg gtg gcc atc cct ggg aat gca agc atg gat gca gtc tgc acg      690
Asn Val Val Ala Ile Pro Gly Asn Ala Ser Met Asp Ala Val Cys Thr
    165                 170                 175 tcc acg tcc ccc acc cgg agt atg gcc cca ggg gca gta cac tta ccc      738
Ser Thr Ser Pro Thr Arg Ser Met Ala Pro Gly Ala Val His Leu Pro
180                 185                 190                 195 cag cca gtg tcc aca cga tcc caa cac acg cag cca act cca gaa ccc      786
Gln Pro Val Ser Thr Arg Ser Gln His Thr Gln Pro Thr Pro Glu Pro
                200                 205                 210 agc act gct cca agc acc tcc ttc ctg ctc cca atg ggc ccc agc ccc      834
Ser Thr Ala Pro Ser Thr Ser Phe Leu Leu Pro Met Gly Pro Ser Pro
            215                 220                 225 cca gct gaa ggg agc act ggc gac ttc gct ctt cca gtt gga ctg att      882
Pro Ala Glu Gly Ser Thr Gly Asp Phe Ala Leu Pro Val Gly Leu Ile
        230                 235                 240 gtg ggt gtg aca gcc ttg ggt cta cta ata ata gga gtg gtg aac tgt      930
Val Gly Val Thr Ala Leu Gly Leu Leu Ile Ile Gly Val Val Asn Cys
    245                 250                 255 gtc atc atg acc cag gtg aaa aag aag ccc ttg tgc ctg cag aga gaa      978
Val Ile Met Thr Gln Val Lys Lys Lys Pro Leu Cys Leu Gln Arg Glu
260                 265                 270                 275 gcc aag gtg cct cac ttg cct gcc gat aag gcc cgg ggt aca cag ggc     1026
Ala Lys Val Pro His Leu Pro Ala Asp Lys Ala Arg Gly Thr Gln Gly
                280                 285                 290 ccc gag cag cag cac ctg ctg atc aca gcg ccg agc tcc agc agc agc     1074
Pro Glu Gln Gln His Leu Leu Ile Thr Ala Pro Ser Ser Ser Ser Ser
            295                 300                 305 tcc ctg gag agc tcg gcc agt gcg ttg gac aga agg gcg ccc act cgg     1122
Ser Leu Glu Ser Ser Ala Ser Ala Leu Asp Arg Arg Ala Pro Thr Arg
        310                 315                 320 aac cag cca cag gca cca ggc gtg gag gcc agt ggg gcc ggg gag gcc     1170
Asn Gln Pro Gln Ala Pro Gly Val Glu Ala Ser Gly Ala Gly Glu Ala
```

-continued

```
              325                 330                 335
cgg gcc agc acc ggg agc tca gat tct tcc cct ggt ggc cat ggg acc    1218
Arg Ala Ser Thr Gly Ser Ser Asp Ser Ser Pro Gly Gly His Gly Thr
340                 345                 350                 355 cag gtc aat gtc acc tgc atc gtg aac gtc tgt agc agc tct gac cac    1266
Gln Val Asn Val Thr Cys Ile Val Asn Val Cys Ser Ser Ser Asp His
                360                 365                 370 agc tca cag tgc tcc tcc caa gcc agc tcc aca atg gga gac aca gat    1314
Ser Ser Gln Cys Ser Ser Gln Ala Ser Ser Thr Met Gly Asp Thr Asp
            375                 380                 385 tcc agc ccc tcg gag tcc ccg aag gac gag cag gtc ccc ttc tcc aag    1362
Ser Ser Pro Ser Glu Ser Pro Lys Asp Glu Gln Val Pro Phe Ser Lys
        390                 395                 400 gag gaa tgt gcc ttt cgg tca cag ctg gag acg cca gag acc ctg ctg    1410
Glu Glu Cys Ala Phe Arg Ser Gln Leu Glu Thr Pro Glu Thr Leu Leu
    405                 410                 415 ggg agc acc gaa gag aag ccc ctg ccc ctt gga gtg cct gat gct ggg    1458
Gly Ser Thr Glu Glu Lys Pro Leu Pro Leu Gly Val Pro Asp Ala Gly
420                 425                 430                 435 atg aag ccc agt taaccaggcc ggtgtgggct gtgtcgtagc caaggtgggc         1510
Met Lys Pro Ser tgagccctgg caggatgacc ctgcgaaggg gccctggtcc ttccaggccc ccaccactag   1570
gactctgagg ctctttctgg gccaagttcc tctagtgccc tccacagccg cagcctccct  1630
ctgacctgca g                                                        1641
```

<210> SEQ ID NO 12
<211> LENGTH: 461
<212> TYPE: PRT
<213> ORGANISM: Human

<400> SEQUENCE: 12

```
Met Ala Pro Val Ala Val Trp Ala Ala Leu Ala Val Gly Leu Glu Leu
        -20                 -15                 -10

Trp Ala Ala His Ala Leu Pro Ala Gln Val Ala Phe Thr Pro Tyr
 -5              -1   1               5                       10

Ala Pro Glu Pro Gly Ser Thr Cys Arg Leu Arg Glu Tyr Tyr Asp Gln
                15                  20                  25

Thr Ala Gln Met Cys Cys Ser Lys Cys Ser Pro Gly Gln His Ala Lys
            30                  35                  40

Val Phe Cys Thr Lys Thr Ser Asp Thr Val Cys Asp Ser Cys Glu Asp
        45                  50                  55

Ser Thr Tyr Thr Gln Leu Trp Asn Trp Val Pro Glu Cys Leu Ser Cys
    60                  65                  70

Gly Ser Arg Cys Ser Ser Asp Gln Val Glu Thr Gln Ala Cys Thr Arg
75                  80                  85                  90

Glu Gln Asn Arg Ile Cys Thr Cys Arg Pro Gly Trp Tyr Cys Ala Leu
                95                  100                 105

Ser Lys Gln Glu Gly Cys Arg Leu Cys Ala Pro Leu Arg Lys Cys Arg
            110                 115                 120

Pro Gly Phe Gly Val Ala Arg Pro Gly Thr Glu Thr Ser Asp Val Val
        125                 130                 135

Cys Lys Pro Cys Ala Pro Gly Thr Phe Ser Asn Thr Ser Ser Ser Thr
    140                 145                 150

Asp Ile Cys Arg Pro His Gln Ile Cys Asn Val Val Ala Ile Pro Gly
155                 160                 165                 170
```

-continued

```
Asn Ala Ser Met Asp Ala Val Cys Thr Ser Thr Ser Pro Thr Arg Ser
            175                 180                 185

Met Ala Pro Gly Ala Val His Leu Pro Gln Pro Val Ser Thr Arg Ser
            190                 195                 200

Gln His Thr Gln Pro Thr Pro Glu Pro Ser Thr Ala Pro Ser Thr Ser
            205                 210                 215

Phe Leu Leu Pro Met Gly Pro Ser Pro Pro Ala Glu Gly Ser Thr Gly
            220                 225                 230

Asp Phe Ala Leu Pro Val Gly Leu Ile Val Gly Val Thr Ala Leu Gly
235                 240                 245                 250

Leu Leu Ile Ile Gly Val Val Asn Cys Val Ile Met Thr Gln Val Lys
            255                 260                 265

Lys Lys Pro Leu Cys Leu Gln Arg Glu Ala Lys Val Pro His Leu Pro
            270                 275                 280

Ala Asp Lys Ala Arg Gly Thr Gln Gly Pro Glu Gln Gln His Leu Leu
            285                 290                 295

Ile Thr Ala Pro Ser Ser Ser Ser Ser Leu Glu Ser Ser Ala Ser
            300                 305                 310

Ala Leu Asp Arg Arg Ala Pro Thr Arg Asn Gln Pro Gln Ala Pro Gly
315                 320                 325                 330

Val Glu Ala Ser Gly Ala Gly Glu Ala Arg Ala Ser Thr Gly Ser Ser
            335                 340                 345

Asp Ser Ser Pro Gly Gly His Gly Thr Gln Val Asn Val Thr Cys Ile
            350                 355                 360

Val Asn Val Cys Ser Ser Ser Asp His Ser Ser Gln Cys Ser Ser Gln
            365                 370                 375

Ala Ser Ser Thr Met Gly Asp Thr Asp Ser Ser Pro Ser Glu Ser Pro
380                 385                 390

Lys Asp Glu Gln Val Pro Phe Ser Lys Glu Glu Cys Ala Phe Arg Ser
395                 400                 405                 410

Gln Leu Glu Thr Pro Glu Thr Leu Leu Gly Ser Thr Glu Glu Lys Pro
            415                 420                 425

Leu Pro Leu Gly Val Pro Asp Ala Gly Met Lys Pro Ser
            430                 435
```

METHOD FOR PRODUCING RECOMBINANT PROTEINS

This Application is a Continuation of U.S. Application Ser. No. 09/225,358, filed Jan. 5, 1999 now abandoned. The disclosure of which is incorporated herein by reference.

FIELD OF THE INVENTION

The present invention relates to a method for producing recombinant proteins, preferably fusion proteins comprising an Fc portion of an immunoglobulin molecule, more preferably fusion proteins comprising an extracellular domain of a tumor necrosis factor receptor fused to the Fc portion of an immunoglobulin molecule. The method of the present invention allows for a reduction of misfolding of the protein, thereby giving rise to a higher yield of the desired protein.

BACKGROUND OF THE INVENTION

Tumor necrosis factor-α (TNFα, also known as cachectin) and tumor necrosis factor-β (TNFβ, also known as lymphotoxin) are homologous mammalian endogenous secretory proteins capable of inducing a wide variety of effects on a large number of cell types. The great similarities in the structural and functional characteristics of these two cytokines have resulted in their collective description as "TNF". Complementary cDNA clones encoding TNFα (Pennica et al, *Nature*, 312:724 (1984); and TNFβ (Gray et al, *Nature*, 312:721 (1984)) have been isolated, permitting further structural and biological characterization of TNF.

TNF proteins initiate their biological effect on cells by binding to specific TNF receptor (TNFR) proteins expressed on the plasma membrane of a TNF-responsive cell. TNFα and TNFβ were first shown to bind to a common receptor on the human cervical carcinoma cell line ME-180 (Aggarwal et al, *Nature*, 318:665 (1985)). Estimates of the size of the TNFR determined by affinity labeling studies ranged from 54 to 175 kDa (Creasey et al, *Proc. Natl. Acad. Sci. USA*, 84:3293 (1987); Stauber et al, *J. Biol. Chem.*, 263:19098 (1988); and Hohmann et al, *J. Biol. Chem.*, 264:14927 (1989)). Although the relationship between these TNFRs of different molecular mass is unclear, Hohmann et al, *J. Biol. Chem.*, 264:14927 (1989)) reported that at least two different cell surface receptors for TNF exist on different cell types. These receptors have an apparent molecular mass of about 75-80 kDa and about 55-60 kDa, respectively. None of the above publications, however, reported the purification to homogeneity of cell surface TNFRs.

In addition to cell surface receptors for TNF, soluble proteins from human urine capable of binding TNF have also been identified (Peetre et al, *Eur. J. Haematol.*, 41:414 (1988); Seckinger et al, *J. Exp. Med.*, 167:1511 (1988); Seckinger et al, *J. Biol. Chem.*, 264:11966 (1989); Seckinger et al, U.K. Patent Publication No. 2,218,101; and Engelmann et al, *J. Biol. Chem.*, 264:11974 (1989)). The relationship of the above soluble urinary binding proteins was further elucidated when the identification and purification of a second distinct soluble urinary TNF binding protein was reported by Engelmann et al, *J. Biol. Chem.*, 265:1531 (1990). The two urinary proteins disclosed by U.K. Patent Publication No. 2,218,101 and the Engelmann et al publications were shown to be immunochemically related to two apparently distinct cell surface proteins by the ability of antiserum against the binding proteins to inhibit TNF binding to certain cells.

More recently, the molecular cloning and expression of a human 55 kDa TNFR (TNFR-I) has been reported (Loetscher et al, *Cell*, 61:351 (1990); Schall et al, *Cell*, 61:361 (1990); and Nophar et al, *EMBO J.*, 9:3269-3278 (1990)). The TNFR of both groups has an N-terminal amino acid sequence which corresponds to the partial amino acid sequence of the urinary binding protein disclosed by U.K. Patent Publication No. 2,218,101; Engelmann et al (1989), supra; and Engelmann et al (1990), supra.

In addition, the molecular cloning and expression of a human 75 kDa TNFR (TNFR-II) has been reported (Smith et al, U.S. Pat. No. 5,395,760; Smith European Patent Publication No. 418014; Smith et al, *Science*, 248:1019-1023 (1990); Dembic et al, *Cytokine*, 2:231-237 (1990); and Kohno et al, *Proc. Natl. Acad. Sci., USA*, 87:8331-8335 (1990).

Smith et al, U.S. Pat. No. 5,395,760 and European Patent Publication No. 418014; as well as Wallach et al, U.S. Pat. No. 5,478,925, disclose multimeric forms of TNFR having enhanced binding affinity for TNF. For example, Smith et al, U.S. Pat. No. 5,395,760 and European Patent Publication No. 418014, disclose a multimeric form of TNFR where one TNFR molecule is linked to another TNFR molecule by a peptide linker (diTNFR), as well as the recombinant production of the same by expressing a gene encoding diTNFR in a transformed host cell.

A particular dimeric form of TNFR is described in Smith et al, U.S. Pat. No. 5,395,760 and European Patent Publication No. 418014, wherein TNFR sequences are substituted for the variable domains of either or both of the immunoglobulin molecule heavy and light chains and having unmodified constant region domains. For example, chimeric TNFR/IgG$_1$ is described which is produced recombinantly using either or both of two chimeric genes——a TNFR/human k light chain chimera (TNFR/C$_k$) and a TNFR/human γ$_1$ heavy chain chimera (TNFR/C$_{γ-1}$). Following transcription and translation of the either chimeric gene in a transformed host, the gene products assemble into a single chimeric antibody molecule having TNFR displayed bivalently.

Jacobs et al, U.S. Pat. No. 5,605,690; Lauffer et al, European Patent Publication No. 464533; Brockhaus et al, European Patent Publication No. 417563; Brockhaus et al, U.S. Pat. No. 5,610,279; Beutler et al, U.S. Pat. No. 5,447,851; Loetscher et al, *J. Biol. Chem.*, 266(27):18324-18329 (1991), Lesslauer et al, *Eur. J. Immunol.*, 21:2883-2886 (1991); Peppel et al, *J. Exp. Med.*, 174(6):1483-1489 (1991); and Mohler et al, *J. Immunol.*, 151:1548-1561 (1993) each disclose chimeric antibodies, wherein an extracellular domain of TNFR is fused to all of the domains of the constant region of a human immunoglobulin heavy chain other than the first domain of said constant region (hereinafter "TNFR:Fc"; or also sometimes referred to in the art as "TNFR-IgG").

TNFR:Fc is useful, inter alia, in diagnostic assays for TNF, as well as in raising antibodies to TNFR for use in diagnosis and therapy. TNFR:Fc is also useful for suppressing TNF-dependent inflammatory responses or diseases in humans, i.e., to bind or scavenge TNF, thereby providing a means for regulating the immune activities of this cytokine. TNF-dependent inflammatory responses or diseases include arthritis, cachexia, endotoxin shock, hypercalcemia, malignancy, inflammatory bowel disease, osteoporosis, endometriosis, myelodysplastic syndrome, and graft vs. host disease. TNFR:Fc is also useful for treatment of insulin and non-insulin dependent diabetes, HIV infection, asthma, multiple sclerosis and congestive heart failure.

The advantage of mammalian expression systems for TNFR:Fc over bacteria and yeast is mammalian secretory pathways facilitate the assembly, folding and production of biologically active proteins. However, as shown in the Examples below, misfolded TNFR:Fc has been found in TNFR:Fc preparations. That is, TNFR:Fc is resolved by hydrophobic interaction chromatography (HIC) into three peaks (FIG. 4). Peak 1 represents truncated forms arising from proteolytic cleavage. Peak 2 consists of highly pure and biologically active TNFR:Fc, while peak 3 is heterogeneous and is comprised of misfolded product along with other process related impurities (FIG. 5). The misfolded TNFR:Fc, which is formed early in the cell culture process, is transported, and represents a significant proportion (about 25-50%) of the expression product. Such misfolded TNFR: Fc is not preferred when TNFR:Fc is used in any of the above-noted therapies. The present invention was developed in view of the discovery of said misfolded TNFR:Fc, and in order to reduce the production of said misfolded TNFR:Fc.

SUMMARY OF THE INVENTION

An object of the present invention is to provide a method for the production of recombinant proteins, e.g., fusion proteins comprising an Fc portion of an immunoglobulin molecule, preferably TNFR:Fc.

An additional object of the present invention is to a method whereby the production of misfolded said recombinant proteins is minimized.

These and other objects of the present invention, which will be apparent from the detailed description of the invention provided hereinafter, have been met, in one embodiment, by a method for producing a recombinant protein so as to reduce protein misfolding comprising culturing a recombinant mammalian host cell which encodes and expresses said recombinant protein so as to produce said recombinant protein, and obtaining the recombinant protein so produced, wherein during a production phase, said host cell is cultured at a temperature of 28-34° C., preferably in the presence of an alkanoic acid or salt thereof.

In a preferred embodiment, the above-described objects of the present invention have been met by a method for producing a fusion protein comprising an Fc portion of an immunoglobulin molecule so as to reduce protein misfolding comprising culturing a recombinant mammalian host cell which encodes and expresses said fusion protein so as to produce said fusion protein, and obtaining the fusion protein so produced, wherein during a production phase, said host cell is cultured at a temperature of 28-34° C., preferably in the presence of an alkanoic acid or salt thereof.

In still another preferred embodiment, the above-described objects of the present invention have been met by a method for producing TNFR:Fc so as to reduce protein misfolding comprising culturing a recombinant mammalian host cell which encodes and expresses TNFR:Fc so as to produce TNFR:Fc, and obtaining the TNFR:Fc so produced, wherein during a production phase, said host cell is cultured at a temperature of 28-34° C., preferably in the presence of an alkanoic acid or salt thereof.

DETAILED DESCRIPTION OF THE INVENTION

Figure 1:
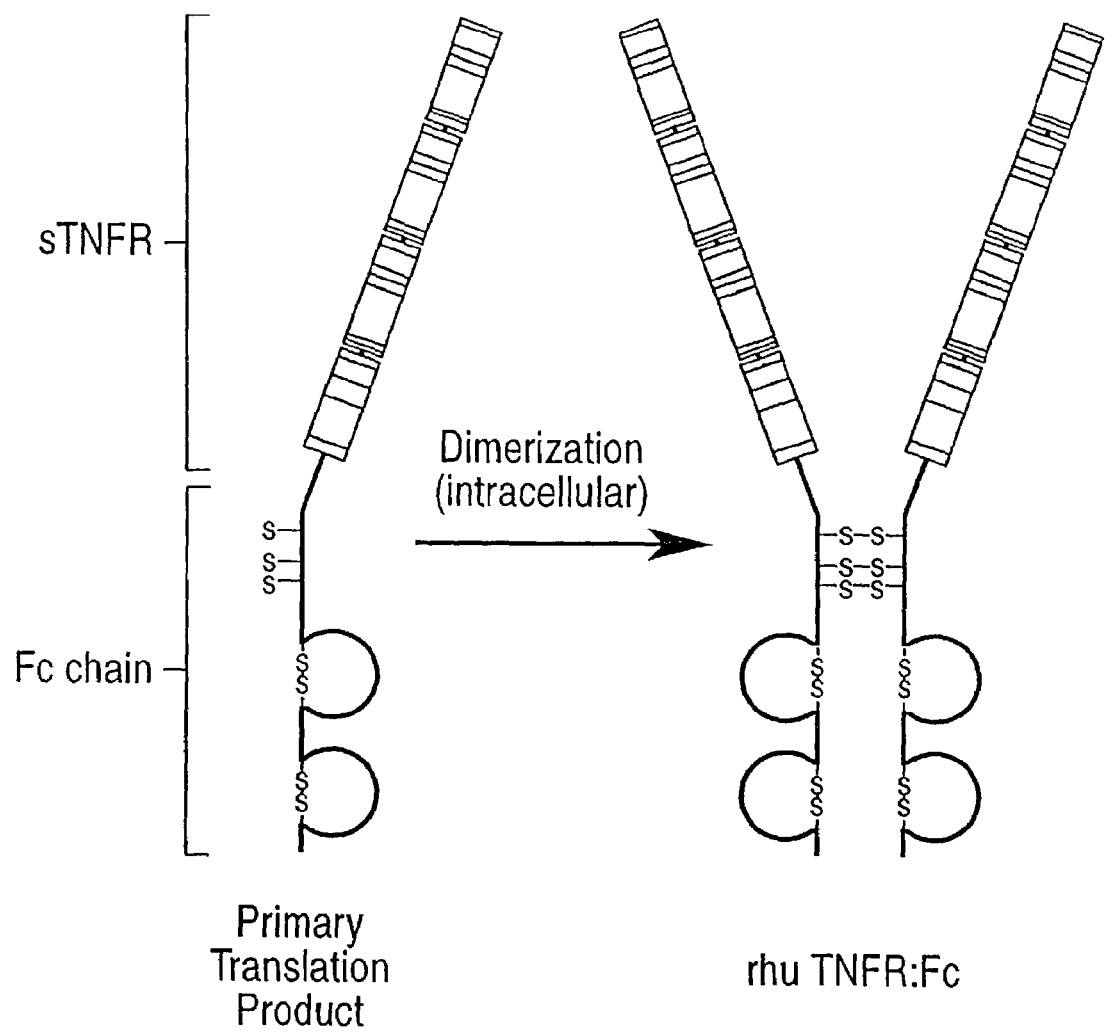
FIG. 1 shows the dimeric structure of the recombinant human TNFR:Fc fusion protein described in the Examples herein. The primary translation product of the plasmid coding for rhuTNFR:Fc is a single molecule of soluble TNFR linked to single chain of Fc derived from human IgG$_1$. Following translation, but prior to secretion, this fusion molecule dimerizes via 3 cysteine residues in the Fc region to form dimeric rhuTNFR:Fc. Boxes denote structural domains of TNFR.

As discussed above, in one embodiment, the above-described objects of the present invention have been met by a method for producing a recombinant protein so as to reduce protein misfolding comprising culturing a recombinant mammalian host cell which encodes and expresses said recombinant protein so as to produce said recombinant protein, and obtaining the recombinant protein so produced, wherein during a production phase, said host cell is cultured at a temperature of 28-34° C., preferably in the presence of an alkanoic acid or salt thereof.

In a preferred embodiment, the above-described objects of the present invention have been met by a method for producing a fusion protein comprising an Fc portion of an immunoglobulin molecule so as to reduce protein misfolding comprising culturing a recombinant mammalian host cell which encodes and expresses said fusion protein so as to produce said fusion protein, and obtaining the fusion protein so produced, wherein during a production phase, said host cell is cultured at a temperature of 28-34° C., preferably in the presence of an alkanoic acid or salt thereof.

In still another preferred embodiment, the above-described objects of the present invention have been met by a method for producing TNFR:Fc so as to reduce protein misfolding comprising culturing a recombinant mammalian host cell which encodes and expresses TNFR:Fc so as to produce TNFR:Fc, and obtaining the TNFR:Fc so produced, wherein during a production phase, said host cell is cultured at a temperature of 28-34° C., preferably in the presence of an alkanoic acid or salt thereof.

I. Definitions

A. Recombinant Protein

The particular recombinant protein which is expressed and produced in the present invention is not critical thereto. Examples of such recombinant proteins include, but are not limited to IL-4R, FLT3L, CD40L, TRAIL, IL-1R type II and TNFR. The recombinant protein is preferably a mammalian glycoprotein.

B. Fusion Protein

The particular fusion protein which is expressed and produced in the present invention is not critical thereto. In the fusion protein, the protein, or biologically active portion thereof is fused to the N-terminal of an Fc portion of an immunoglobulin molecule. The Fc portion contains the $CH_2$ and $CH_3$ domains of an immunoglobulin molecule, and at least a portion of the hinge region of the immunoglobulin molecule, preferably the entire hinge region. Examples of such fusion proteins include, but are not limited to human receptor activator of NF-KappaB (huRANK:Fc) and tunica internal endothelial cell kinase-delta:Fc (TEKdelta:Fc), and TNFR:Fc.

C. TNFR

The particular TNFR employed is not critical to the present invention and may be selected from any mammalian TNFR, e.g., murine TNFR; the 75 kilodalton (kDa) human TNFR described in U.S. Pat. No. 5,395,760; which is incorporated by reference herein in its entirety, or the 55 kDa human TNFR described in U.S. Pat. No. 5,610,279, which is incorporated by reference herein in its entirety.

As used herein, the term "TNFR" refers to proteins having amino acid sequences which are substantially similar to the native mammalian TNFR amino acid sequences, and which are biologically active, as defined below, in that they are capable of binding TNF molecules or transducing a biological signal initiated by a TNF molecule binding to a cell, or cross-reacting with anti-TNFR antibodies raised against TNFR from natural (i.e., nonrecombinant) sources.

Figure 2:
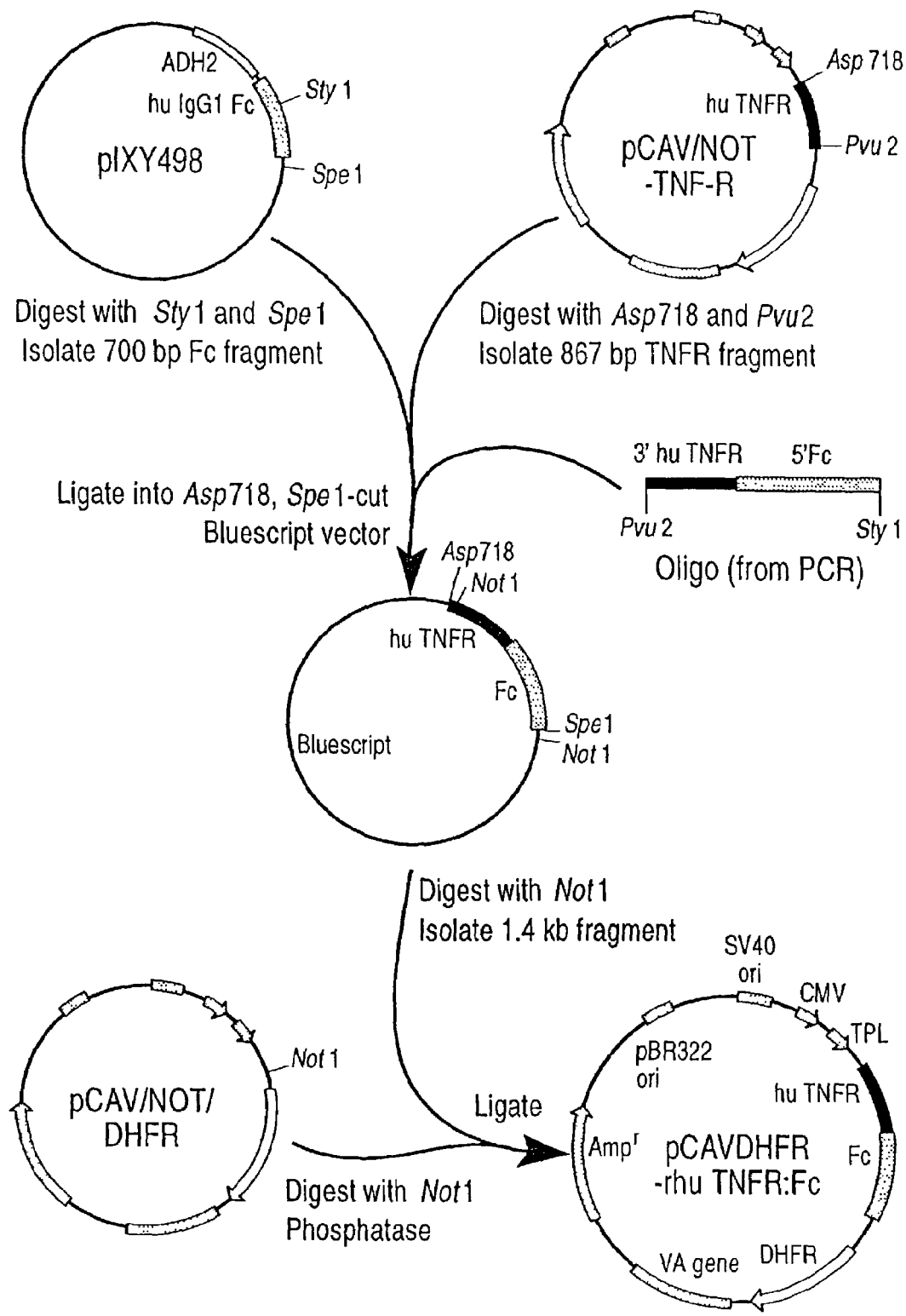
FIG. 2 shows the construction of plasmid pCAVDHFR-rhuTNFR:Fc. Abbreviations are as follows: ADH2, yeast alcohol dehydrogenase gene and regulatory region; SV40, simian virus 40 early region promoter; CMV, cytomegalovirus immediate early enhancer; TPL, adenovirus-2 tripartite leader; VA, adenovirus-2 virus-associated RNA genes I and II; Amp$^r$, ampicillin resistance gene; DHFR, hamster dihydrofolate reductase gene; ORI, bacterial origin of replication.

The mature full-length of the two human TNFRs are glycoproteins having a molecular weight of about 55 kDa and 75 kDa (hereinafter TNFR-I and TNFR-II, respectively). As used throughout the specification, the term "mature" means a protein expressed in a form lacking a leader sequence as may be present in full-length transcripts of a native gene. The term "TNFR" includes, but is not limited to, analogs or subunits of native proteins having at least 20 amino acids and which exhibit at least some biological activity in common with TNFR, for example, soluble TNFR constructs which are devoid of a transmembrane region (and are secreted from the cell) but retain the ability to bind TNF. Various bioequivalent protein and amino acid analogs are described in detail below. The nomenclature for TNFR analogs as used herein follows the convention of naming the protein (e.g., TNFR preceded by either hu (for human) or mu (for murine) and followed by a Δ (to designate a deletion) and the number of the C-terminal amino acid. For example, huTNFR-IIΔ235 referes to human TNFR-II having $Asp^{235}$ as the C-terminal amino acid (i.e., a polypeptide having the sequence of amino acids 1-235 of FIG. 2A of U.S. Pat. No. 5,395,760 (SEQ ID NOs. 11 and 12)). In the absence of any human or murine species designation, TNFR refers generically to a mammalian TNFR, as well as to either human TNFR-I or or TNFR-II. Similarly, in the absence of any specific designaton for deletion mutants, the term TNFR means all forms of TNFR, including mutants and analogs which possess TNFR biological activity.

"Soluble TNFR" or "STNFR" as used in the context of the present invention refer to proteins, or substantially equivalent analogs, having an amino acid sequence corresponding to all or part of the extracellular region of a native TNFR, for example, huTNFR-IIΔ235, huTNFR-IIΔ185 and huTNFR-IIΔ163, or amino acid sequences substantially similar to the sequences of amino acids 1-163, amino acids 1-185, or amino acids 1-235 of FIG. 2A of U.S. Pat. 5,395,760, and which are biologically active in that they bind to TNF ligand. Equivalent soluble TNFRs include polypeptides which vary from these sequences by one or more substitutions, deletions, or additions, and which retain the ability to bind TNF or inhibit TNF signal transduction activity via cell surface bound TNF receptor proteins, for example huTNFR-IIΔx, wherein x is selected from the group consisting of any one of amino acids 163-235 of FIG. 2A of U.S. Pat. No. 5,395,760. Analogous deletions may be made to huTNFR-I and muTNFR.

As to huTNFR-I, a DNA sequence which codes, for example, a non-soluble protein fragment extends from nucleotide-185 to 1122 of the sequence given in FIGS. 1A-1B of U.S. Pat. No. 5,160,279 (SEQ ID NOs. 9 and 10). DNA sequences which code for soluble protein fragments thereof are, for example, those which extend from nucleotide -185 to 633 or from nucleotide -14 to 633 of the sequence given in said FIGS. 1A-1B.

Included with the TNFR of the present invention are those whose amino acids have been exchanged, for example by planned mutagenesis, so that the activity of the TNFR, namely the binding of TNF or the interaction with other membrane components participating in the signal transfer, have been altered or maintained in a desired manner. Amino acid exchanges in proteins which do not generally alter the activity of such molecules are known in the art and are described, for example, by Neurath et al, *The Proteins*, Academic Press, New York (1979) (see especially FIG. 6, page 14 thereof). The most commonly occurring exchanges are: Ala/Ser, Val/Ile, Asp/Glu, Thr/Ser, Ala/Gly, ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

Inhibition of TNF signal transduction activity can be determined by transfecting cells with recombinant TNFR DNAs to obtain recombinant receptor expression. The cells are then contacted with TNF and the resulting metabolic effects examined. If an effect results which is attributable to the action of the ligand, then the recombinant receptor has signal transduction activity. Exemplary procedures for determining whether a polypeptide has signal transduction activity are disclosed by Idzerda et al, *J. Exp. Med.*, 171:861 (1990); Curtis et al, *Proc. Natl. Acad. Sci. USA*, 86:3045 (1989); Prywes et al, *EMBO J.*, 5:2179 (1986); and Chou et al, *J. Biol. Chem.*, 262:1842 (1987). Alternatively, primary cells or cell lines which express an endogenous TNF receptor and have a detectable biological response to TNF could also be utilized.

D. Fc portion

As discussed above, as used herein, Fc portion of an immunoglobulin molecule refers to at least a portion of the hinge region, $CH_2$ domain, and $CH_3$ domain thereof, i.e., such does not include the $CH_1$ domain.

The particular immunoglobulin molecule from which the immunoglobulin heavy chain is derived is not critical to the present invention. Examples of such immunoglobulin molecule may be selected from the group consisting of IgG, IgM, IgA and IgE. The immunoglobulin heavy chain is preferably IgG, e.g., $IgG_1$ or $IgG_3$.

II. Expression of Recombinant Proteins

The present invention provides recombinant expression vectors to amplify or express DNA encoding recombinant proteins, e.g., encoding a fusion protein comprising an Fc portion of an immunoglobulin molecule, more preferably TNFR:FC. Recombinant expression vectors are replicable DNA constructs which have synthetic or cDNA-derived DNA fragments encoding the recombinant protein, e.g., a fusion protein, such as TNFR:Fc or bioequivalent analogs operably linked to suitable transcriptional or translational regulatory elements derived from mammalian genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements may include an operator sequence to control transcription, a sequence encoding suitable mRNA ribosomal binding sites. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

Transformed host cells are cells which have been transformed or transfected with the vectors constructed using recombinant DNA techniques. Transformed host cells ordinarily express the recombinant protein, e.g., the fusion protein such as TNFR:Fc, but host cells transformed for purposes of cloning or amplifying recombinant protein, e.g., the fusion protein, such as TNFR:Fc, DNA do not need to express the same. Expressed recombinant protein will be secreted into the culture supernatant. Suitable host cells for expression of recombinant protein, fusion protein or mammalian TNFR:Fc include higher eukaryotic cells, e.g., established cell lines of mammalian origin as described below. Appropriate cloning and expression vectors for use with mammalian cellular hosts are described by Pouwels et al, *Cloning Vectors: A Laboratory Manual*, Elsevier, New York (1985), the relevant disclosure of which is hereby incorporated by reference.

Various mammalian cell culture systems are advantageously employed to express recombinant protein, fusion protein or TNFR:Fc. Expression of recombinant proteins in mammalian cells is particularly preferred because such proteins are generally correctly folded, appropriately modified and completely functional. Examples of suitable mammalian host cell lines include the COS-7 lines of monkey kidney cells, described by Gluzman, *Cell,* 23:175 (1981), and other cell lines capable of expressing an appropriate vector including, for example, L cells, C127, 3T3, Chinese hamster ovary (CHO), HeLa and BHK cell lines. Mammalian expression vectors may comprise nontranscribed elements, such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al, *Nature,* 273:113 (1978)). Smaller or larger SV40 fragments may also be used, provided the approximately 250 bp sequence extending from the HindIII site toward the Bgl I site located in the viral origin of replication is included. Further, a mammalian genomic promoter, such as the TNFR promoter, control and/or signal sequences may be utilized, provided such control sequences are compatible with the host cell chosen. Exemplary vectors can be constructed as disclosed by Okayama et al, *Mol. Cell. Diol.,* 3:280 (1983).

A useful system for stable high level expression of mammalian cDNAs in C127 murine mammary epithelial cells can be constructed substantially as described by Cosman et al, *Mol. Immunol.,* 23:935 (1986).

In preferred aspects of the present invention, recombinant expression vectors comprising the recombinant protein, e.g., the fusion protein such as TNFR:Fc encoding DNA is stably integrated into a host cell's DNA. Elevated levels of expression product is achieved by selecting for cell lines having amplified numbers of vector DNA. Cell lines having amplified numbers of vector DNA are selected, for example, by transforming a host cell with a vector comprising a DNA sequence which encodes an enzyme which is inhibited by a known drug. The vector may also comprise a DNA sequence which encodes a desired protein. Alternatively, the host cell may be co-transformed with a second vector which comprises the DNA sequence which encodes the desired protein. The transformed or co-transformed host cells are then cultured in increasing concentrations of the known drug, thereby selecting for drug-resistant cells. Such drug-resistant cells survive in increased concentrations of the toxic drug by over-production of the enzyme which is inhibited by the drug, frequently as a result of amplification of the gene encoding the enzyme. Where drug resistance is caused by an increase in the copy number of the vector DNA encoding the inhibitable enzyme, there is a concomitant co-amplification of the vector DNA encoding the desired recombinant protein, e.g., the fusion protein such as TNFR:Fc, in the host cell's DNA.

A preferred system for such co-amplification uses the gene for dihydrofolate reductase (DHFR), which can be inhibited by the drug methotrexate (MTX). To achieve co-amplification, a host cell which lacks an active gene encoding DHFR is either transformed with a vector which comprises DNA sequence encoding DHFR and a desired protein, or is co-transformed with a vector comprising a DNA sequence encoding DHFR and a vector comprising a DNA sequence encoding the desired protein. The transformed or co-transformed host cells are cultured in media containing increasing levels of MTX, and those cell lines which survive are selected.

A particularly preferred co-amplification system uses the gene for glutamine synthetase (GS), which is responsible for the synthesis of glutamate and ammonia using the hydrolysis of ATP to ADP and phosphate to drive the reaction. GS is subject to inhibition by a variety of inhibitors, for example methionine sulphoximine (MSX). Thus, the recombinant protein, e.g., the fusion protein such as TNFR:Fc can be expressed in high concentrations by co-amplifying cells transformed with a vector comprising the DNA sequence for GS and a recombinant protein, e.g., the fusion protein, such as TNFR:Fc, or co-transformed with a vector comprising a DNA sequence encoding GS and a vector comprising a DNA sequence encoding a recombinant protein, e.g., the fusion protein such as TNFR:Fc, culturing the host cells in media containing increasing levels of MSX and selecting for surviving cells. The GS co-amplification system, appropriate recombinant expression vectors and cells lines, are described in the following PCT applications: WO 87/04462, WO 89/01036, WO 89/10404 and WO 86/05807.

Recombinant protein or fusion protein or TNFR:Fc are preferably expressed by co-amplification of DHFR or GS in a mammalian host cell, such as Chinese Hamster Ovary (CHO) cells, or alternatively in a murine myeloma cell line, such as SP2/0-Ag14 or NS0 or a rat myeloma cell line, such as YB2/3.0-Ag20, disclosed in PCT applications WO/89/10404 and WO 86/05807.

Preferred eukaryotic vectors for expression of TNFR:Fc DNA are disclosed in Example 1 below. One of these vectors, referred to as pCAV/NOT, was derived from the mammalian high expression vector pDC201 and contains regulatory sequences from SV40, Adenovirus-2, and human cytomegalovirus.

Specific examples of TNFR:Fc can be constructed as described in Example 1 below, as well as in Jacobs et al, U.S. Pat. No. 5,605,690; Lauffer et al, European Patent Publication No. 464533; Brockhaus et al, European Patent Publication No. 417563; Brockhaus et al, U.S. Pat. No. 5,610,279; Beutler et al, U.S. Pat. No. 5,447,851; Etcheverry et al, U.S. Pat. No. 5,705,364; Etcheverry et al, U.S. Pat. No. 5,721,121; Loetscher et al, *J. Biol. Chem.*, 266 (27) :18324-18329 (1991), Lesslauer et al, *Eur. J. Immunol.*, 21:2883-2886 (1991); Peppel et al, *J. Exp. Med.*, 174(6):1483-1489 (1991); and Mohler et al, *J. Immunol.*, 151:1548-1561 (1993). The preferred TNFR:Fc contains the extracellular domain of TNFR-II, i.e., TNFR-II:Fc, which can be constructed as described in Example 1 below.

III. Purification of Recombinant Proteins

Purified recombinant protein, e.g., the fusion protein such as TNFR:Fc is prepared by culturing suitable host/vector systems to express the recombinant translation products of the DNAs encoding the same, which are then purified from culture media or cell extracts.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise a TNF or lectin or protein A Sepharose or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify a TNFR composition. Some or all of the foregoing purification steps, in various combinations, can also be employed to provide a homogeneous recombinant protein.

Recombinant protein, e.g., the fusion protein such as TNFR:Fc synthesized in recombinant culture is characterized by the presence of non-human cell components, including proteins, in amounts and of a character which depend upon the purification steps taken to recover recombinant protein or fusion protein or TNFR:Fc from the culture. These components ordinarily will be of non-human higher eukaryotic origin and preferably are present in innocuous contaminant quantities, on the order of less than about 1 percent by weight. Further, recombinant cell culture enables the production of recombinant protein, e.g., the fusion protein such as TNFR:Fc free of proteins which may be normally associated with therewith, e.g., normally associated with TNFR as it is found in nature in its species of origin, e.g., in cells, cell exudates or body fluids.

The recombinant host cells are generally first cultured at a temperature which promotes exponential logarithmic growth of the cells, prior to entering into the production phase. The temperature during this so-called "growth phase" is generally 34 to 38° C., preferably 37° C. The growth phase generally is carried out for a period of about 3 to 7 days, preferably about 4 to 5 days.

The term "production phase" as used herein refers to the period during which cell growth has plateaued, i.e., logarithmic cell growth has ended, and protein production is primary. The temperature during the production phase is generally 28-34° C., preferably 25-30° C., more preferably 26-29° C., still more preferably 27-28° C. The particularly preferred temperature during the production phase is 28° C. The production phase is generally carried out for a period of about 8 to 14 days, preferably about 10 to 12 days.

The production phase may be proceeded by a "transition phase" wherein the temperature is lowered to about between 28-34° C. Generally, the transition phase is carried out for between 24 and 48 hrs prior to entering into the production phase.

The alkanoic acid or salt thereof is employed in order to enhance the production of recombinant protein. The alkanoic acid employed is a straight or branched chain, saturated or unsaturated alkanoic acid or salt thereof, generally having from 1-10 carbon atoms, preferably from 3-6 carbon atoms. The particular alkanoic acid or salt thereof employed is not critical to the present invention. Examples of alkanoic acids or salts thereof which can be employed in the present invention include butyric acid, sodium butyrate or dibutyryl cAMP. The amount of alkanoic acid employed is also not critical to the present invention. Generally the amount of alkanoic acid or salt thereof which is employed in the present invention is in the range of 0.1-5.0 mM, preferably 0.25-2.0 mM.

The alkanoic acid may be added to the culture prior to entering into the production phase. Generally, such a "transition phase", is carried out for 24-48 hrs prior to entering into the production phase.

The particular osmolality under which the host cells are cultured in the growth phase is not critical thereto. Generally, the osmolality is in the range of 200 to 400 mOsm, preferably 250 to 350 mOsm.

The particular osmolality under which the host cells are cultured in the production phase is not critical thereto. Generally, the osmolality is in the range of 200 to 400 mOsm, preferably 250 to 350 mosm.

Generally, in the growth phase the dissolved oxygen should be between about 20-80%, and the pH of the culture medium should be about 6.6-7.4, preferably about 6.8-7.4.

Generally, in the production phase the dissolved oxygen should be between about 20-80%, and the pH of the culture medium should be about 6.6-7.4, preferably about 6.8-7.4.

The growth phase may be carried out as a batch or perfusion, preferably perfusion.

The production phase may be carried out as a batch or fed batch.

IV. Therapeutic Administration of Recombinant Proteins

Therapeutic compositions comprising an effective amount of recombinant protein, e.g., the fusion protein such as TNFR:Fc and a suitable diluent and carrier, and methods for suppressing TNF-dependent inflammatory responses in humans can be achieved by administering an effective amount of TNFR:Fc.

For therapeutic use, purified recombinant protein, e.g., the fusion protein such as TNFR:Fc is administered to a patient, preferably a human, for treatment in a manner appropriate to the indication. Thus, for example, compositions containing the same can be administered by bolus injection, continuous infusion, sustained release from implants, or other suitable technique. Typically, the recombinant protein, e.g., the fusion protein such as TNFR:Fc will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the recombinant protein, e.g., the fusion protein such as TNFR:Fc with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

The dosage to be administered will vary depending upon the age, weight and sex of the subject being treated, as well as the condition being treated. Generally, the dosage of TNFR:Fc administered will be at least about 4.0 mg iv per subject twice a week, preferably about 4.0 to 100 mg iv per subject twice a week.

TNFR:Fc is administered for the purpose of inhibiting TNF-dependent responses. A variety of diseases or conditions are believed to be caused by TNF, such as, arthritis, cachexia and septic shock. In addition, other key cytokines (IL-1, IL-2 and other colony stimulating factors) can also induce significant host production of TNF. TNFR:Fc compositions may therefore be used, for example, to treat arthritis, cachexia or septic shock hypercalcemia, malignancy, inflammatory bowel disease, osteoporosis, endometriosis, myelodysplastic syndrome, and graft vs. host disease, or to treat side effects associated with cytokine therapy. Because of the primary roles IL-1 and IL-2 play in the production of TNF, combination therapy using both IL-1 receptors or IL-2 receptors may be preferred in the treatment of TNF-associated clinical indications. TNFR:Fc is also useful for treatment of insulin and non-insulin dependent diabetes, HIV infection, asthma, multiple sclerosis and congestive heart failure.

Uses of the other recombinant proteins or fusion proteins of the present invention will depend on the protein, and will be readily apparent to those skilled in the art.

The following examples are provided for illustrative purposes only, and are in no way intended to limit the scope of the present invention.

EXAMPLE 1

Construction and Expression of Soluble Human TNFR:Fc

The cloning of the DNA for TNFR-II has been described in detail in Smith et al, *Science*, 248:1019 (1990).

A. Preparation of the 2A5-3 Cell Line

1. Construction of pCAVDHFRrhuTNFR:Fc

A schematic diagram showing the construction of the recombinant soluble human TNFR:Fc expression vector, designated pCAVDHFRrhuTNFR:Fc, is shown in FIG. 1. The rhuTNFR:Fc fusion gene was created by ligating the following fragments into Bluescript®, a commercially available cloning vector (Stratagene):

(1) an 867 bp Asp718-PuvII fragment from pCAV/NOT-TNFR (ATCC 68088) containing the cDNA encoding TNFR-IIΔ235.

(2) A 700 bp StyI-SpeI fragment from plasmid pIXY498 coding for 232 amino acids of the Fc portion of human IgG$_1$. Plasmid pIXY498 is a yeast expression vector containing the Fc fragment of human IgG$_1$, (see FIG. 2).

(3) An oligonucleotide linker, to fuse the truncated TNFR-II with the human IgG$_1$, Fc fragment. This linker was created by PCR (polymerase chain reaction) amplification using two primers, one having the sequence CCCCAGCTGAAGGGAGCACTGGCGAC-GAGCCCAAATCTTGTGACAAAACTC (SEQ ID NO:1), which encodes the 3' end of the TNFR-IIΔ235 and the 5' end of human IgG$_1$, and the other having the sequence CGGTACGTGCTGTTGTTACTGC (SEQ ID NO:2), an antisense sequence encoding nucleotides 257-237 of human IgG$_1$. The template for this reaction was pIXY498. The reaction product was digested with PvuIII and StyI, and a 115 bp fragment was isolated.

This construct was then digested with NotI and the resulting 1.4 kb DNA fragment containing the rhuTNFR:Fc fusion DNA sequence was ligated into the NotI site of plasmid pCAV/NOT/DHFR. Plasmid pCAV/NOT/DHFR was derived from plasmid pCAV/NOT by inserting the hamster dihydrofolate reductase DNA sequence (DHFR) into the HpaI site of pCAV/NOT (ATCC 68014). This construct was designated plasmid pCAVDHFRrhuTNFR:Fc. The entire coding region sequence was confirmed by DNA sequencing, and the TNFR-II:Fc DNA and amino acid sequences therein is shown in SEQ ID NOs:3 and 4, respectively.

2. Preparation of Host Strain and Transfection

To prepare the host strain, DXB-11 CHO cells deficient in the expression of dihydrofolate reductase (DHFR) were obtained from Dr. Lawrence Chasin at Columbia University.

A bank of 100 vials of these cells were established, and representative vials were sent to Microbiological Associates for examination via the procedures shown in Table 1 below:

TABLE 1

| | Test | Result |
|---|---|---|
| 1. | Transmission Electron Microscopy (TEM) | Type A only |
| 2. | Sterility - Bacterial and Fungal | negative |
| 3. | Mycoplasma | negative |
| 4. | Mouse Antibody Production (MAP) | negative |

All transfections and amplification steps were performed in a separate laboratory set aside for this purpose. Only mycoplasma-free cell lines were allowed into this facility.

Transfections were performed by mixing pCAVDHFR-rhuTNFR:Fc plasmid DNA with Lipofectin™ reagent from Gibco BRL. Approximately, 10 μg of DNA was added to 10 cm petri dishes containing 2×10⁶ CHO DXB-11 cells. After the initial transfection, cells were selected for the expression of DHFR by subculturing in selective medium lacking glycine, hypoxanthine and thymidine. The resulting colonies were then transferred to 24-well plates and analyzed for rhuTNFR:Fc expression as disclosed by Sims et al, *Science*, 241:585 (1988). More specifically, 3.0 ml of binding medium containing $1.2 \times 10^{-11}$ $M^{125}$I-labeled FLAG®-TNF was added to each plate and the plates incubated at 4° C. for 120 min. This medium was then discarded, and each plate was washed once with cold binding medium (containing no labeled TNF) and twice with cold PBS. The edges of each plate were then broken off, leaving a flat disk which was contacted with X-ray film for 72 hrs at −70° C. using an intensifying screen. TNF binding activity was visualized on the exposed films as a dark focus against a relatively uniform background. The highest expressing cultures were subjected to amplification by exposure to increasing concentrations of methotrexate (MTX). Cells able to grow at 25 nM MTX were cloned by limiting dilution in 96-well plates. The highest expressing clones were transferred to suspension culture and the final selection of clone 4-4FC102A5-3 was made based on its high level of rhuTNFR-II:Fc expression under these conditions. This cell line will hereinafter be referred to as the "2A5-3 cell line".

B. Preparation of the VA12 Cell Line

1. Construction of p2A5IaTNFR:Fc

Figure 3:
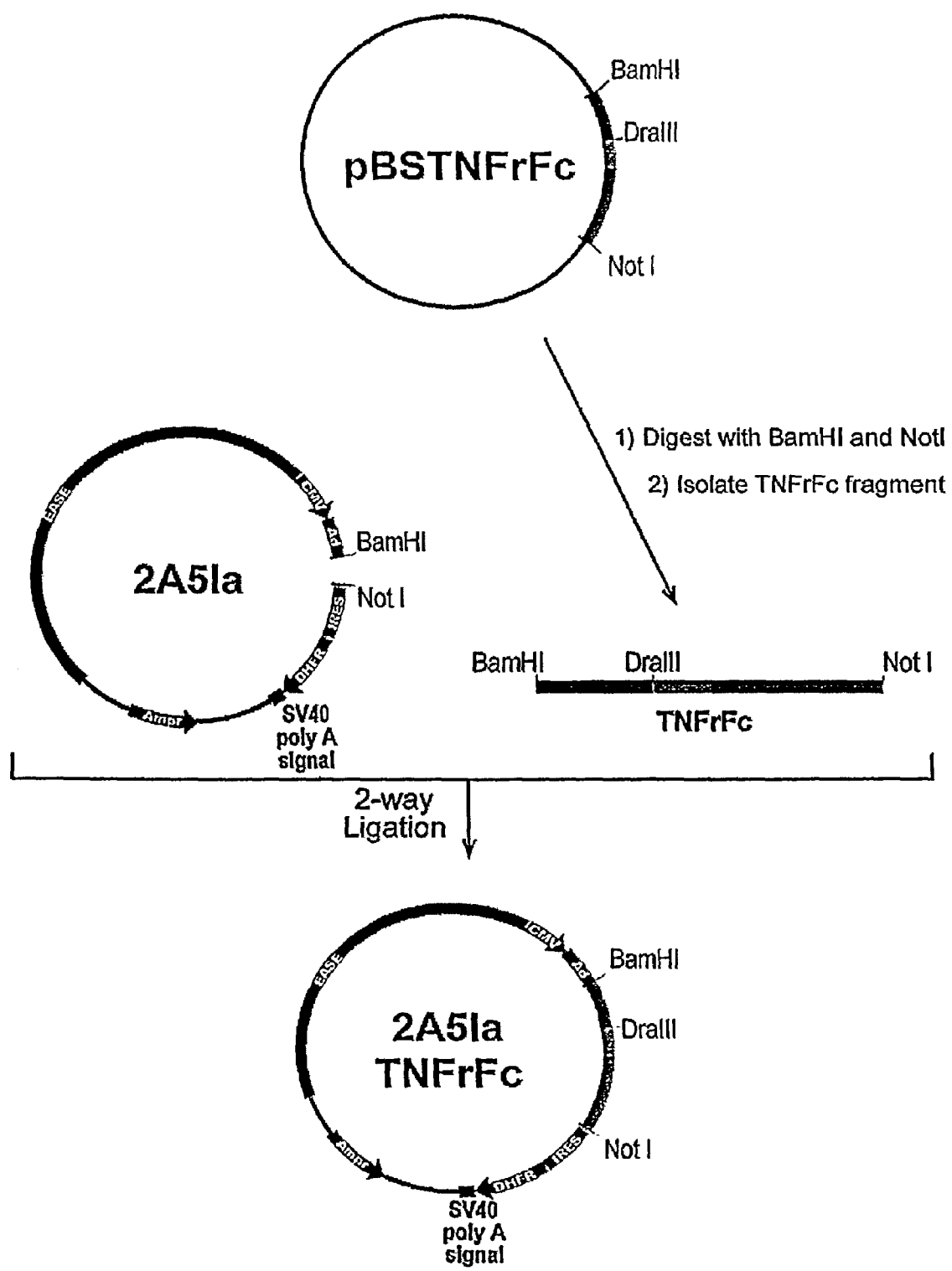
FIG. 3 shows the construction of plasmid p2A5IaTNFR: Fc. Abbreviations are as follows: CMV, cytomegalovirus immediate early enhancer; Ad, adenovirus-2 tripartite leader; VA, IRES, encephalomyocarditis virus internal ribosomal entry site; DHFR, hamster dihydrofolate reductase gene; SV40, simian virus 40; AMp$^r$, ampillicin resistance gene; EASE, expression augmenting sequence element from CHO cells.

A schematic diagram showing the construction of the recombinant soluble human TNFR:Fc expression vector, designated p2A5IaTNFR:Fc, is shown in FIG. 3.

More specifically, pCAVDHFRrhuTNFR:Fc was digested with DraIII and NotI, which released a DraIII-NotI fragment encoding the carboxy portion of TNFR and the Fc portion of TNFR:Fc. A fragment encoding a Kozak sequence for improved translation, as well as the N-terminus of TNFR, was PCR amplified using the following primers: 5'-ATCA-CACACGGTGTCCGAGGTCTTGGTACAGAAGAC-3' (SEQ ID NO:5) and 5'-ATCTAGGATCCGCCGCCAC-CATGGCGCCCGTCGCCGTCTG-3'(SEQ ID NO:6), and the TNFR:Fc fragment as template. The PCR fragment generated was digested with BamHI and DraIII, and subcloned with the DraIII-NotI fragment into pBluescript (La Jolla, Calif.). The resulting plasmid, pBSTNFR:Fc (see FIG. 3), contained the complete coding sequence for TNFR:Fc along with a 5' Kozak sequence. Subsequently, the TNFR:Fc coding sequence was isolated from pBSTNFR:Fc using BamHI and NotI digestion, and cloned into 2A5Ia that had been digested with NotI and BamHI (see FIG. 3).

2A5Ia is a derivative of PG5.7 and consists of: a NotI-MamI fragment from pCDE (Brasel et al, *Blood*, 88:2004 (1996)) containing the encephalomyocarditis virus internal ribosomal entry site (IRES), and part of the hamster dhfr coding sequence that was cloned into the NotI-MamI site of PG5.7. A multiple cloning site was added to the resulting modified PG5.7 by addition of annealed oligonucleotides to the NotI-XmaI sites of the modified PG5.7. The oligonucleotides used to construct the multiple cloning site were: 5'-CCGGTTTAAACGTCGACATCCCGGGATC-CTAGGATCCGGATCGATCGGAC CGCGGCCGCGTT-TAAAC-3' (SEQ ID NO:7), and 5'-GGCCGTT-TAAACGCGGCCGCGGTCCGATCGATCCGGATCCTA GGATCCCG GGATGTCGACGTTTAAA-3' (SEQ ID NO:8).

PG5.7 consists of DNA fragments from 2A5-3λ DNA cloned into the EcoRI-SalI site of PGEMI (Promega).

2A5-3λk DNA was isolated from a CHO cell genomic library as follows: A transformed CHO cell line (designated as the "2A5-3 cell line") expressing high levels of an immunoglobulin Fc fusion protein comprising the extracellular domain of the 75 kDa TNFR (TNFR:Fc; Mohler et al, *J. Immunol.*, 151:1548 (1993); and U.S. Pat. No. 5,395,760, issued Mar. 7, 1995; the disclosure of both of which are incorporated by reference) was selected for preparation of a genomic library since Southern blot analysis indicated that the high expression of TNFR:Fc expression observed for this cell line is driven by a single integration of an expression cassette encoding TNFR:Fc. DNA was isolated from these cells, partially digested with MboI and cloned into a lambda FIX II cloning vector (Stratagene custom genomic library; Stratagene La Jolla, Calif.) to form a library. The TNFR coding sequence, along with 14.4 kb of cellular flanking sequences, was cloned from the library as described below.

To screen the library; approximately $2.0 \times 10^4$ plaque forming units (pfu) were allowed to form per 250 cm plate. Plaques were transformed to nitrocellulose membranes (Schleicher and Schuell, Keene, N.H.) and lysed using standard protocols supplied by Stratagene. The filters were probed with a random primed Not1-PvuII DNA fragment encoding a cell surface portion of TNFR extracellular domain (Mohler et al, supra). Hybridizations were preformed at 63° C. in hybridization buffer comprising 10×Denhart's solution, 0.05 M Tris (pH 7.5), 1.0 M NaCl, 0.1% (w/v) sodium pyrophosphate, 1.0% (w/v) SDS, and 4.0 μg/ml salmon sperm DNA (Maniatis, *Molecular Cloning: A Laboratory Manual*, Cold Spring Harbor Laboratory). Filters were washed as follows: initial wash in 0.1% (w/v) SDS, 0.1% (v/v) SSC at 42° C. for 30 min, followed by two additional washes in the same solution for 60 min at 63° C. (Maniatis, supra). The final two washes were at 63° C. for 60 min using 0.1% (w/v) SDS and 0.01% (v/v) SSC. A single positive recombinant clone was identified after screening about $1.0 \times 10^5$ recombinants. This clone was designated 2A5-3λk. 2A5-3λ was deposited with the American Type Culture Collection, Rockville, Md., under the terms of the Budapest Treaty on Jan. 4, 1996, and given accession number 97411.

To make PG5.7, the 3' SalI-EcoRI fragment of 2A5-3λ, including the TNFR:Fc expression cassette, the CMV promoter enhancer, DHFR cDNA and the adenovirus-2 tripartite leader sequence, was cloned into the SalI-EcoRI sites of pGEMI to make PG2.2. Subsequently, the EcoRI fragment of 2A5-3λ immediately 5' to the SalI-EcoRI was inserted into the unique EcoRI site of PG2.2 to make PG5.7.

2. Preparation of Host Strain and Transfection p2A5IaTNFR:Fc was used to transfect a derivative of DXB-11 CHO cells (Urlaub et al, *Proc. Natl. Acad. Sci., USA*, 77:4216-4220 (1980)) that had been adapted to growth in serum-free media comprising IMX1.2 media, supplemented with 100 ng/ml of LongR$^3$ IGF-1 (IGF-1) (GroPep, Adelaide, Australia), 100 µg/ml of bovine transferrin (transferrin) (JRH, Kansas City), 2.0 mM L-glutamine, 90 µM thymidine, 90 µM hypoxanthine and 120µM glycine. The composition of IMX1.2 media is shown in Table 2 below. CHO cells were transfected with Lipofectin™ reagent from Gibco BRL using conditions recommended by the supplier for suspension cultures. After selection in growth media comprising IMX1.2 media, supplemented with 100 ng/ml of IGF-1, 100 µg/ml of transferrin, 6.0 mM L-glutamine and 1.0 mM aspargine, without glycine, hypoxanthine or thymidine (-GHT), cell pools were grown in the same media containing 50 nM methotrexate (MTX) (Lederle, Perle River, N.J.). After several passages in this media, pools were grown in the same media containing 150 nM MTX. Pools grown in 150 nM MTX were screened for production of TNFR:Fc and the best pool, 150B was cloned using a soft agar method (Gibson et al, *BioTechniques*, 15(4):594 (1993); Gibson et al, *BioTechniques*, 15(4):597 (1993); and Gibson et al, *Methods Mol. Biol.*, 63(*Recombinant Protein Protocols*):77-83 (1997)).

Production of TNFR:Fc was monitored by an antibody sandwich enzyme-linked immunosorbent assay (ELISA) as described in Engvall et al, *G. Immunochemistry* (England), 8:871-874 (1971). For detection of TNFR:Fc, two monoclonal antibodies (mAb) against different epitopes of TNFR:Fc were used. The first mAb (a mouse IgG$_1$ raised against the 75 kDa TNFR) was adsorbed into 96 well plates overnight, and the peroxidase (HRP) conjugated second antibody (a rat IgG$_{2b}$ raised against the 75 kDa TNFR (Genzyme)) was added after a wash step. In several experiments quantities of between 0.78 and 50 ng/ml TNFR:Fc were detected.

The soft agar clones were screened for TNFR:Fc protein production as described above and the best clone, 150B-8 was re-cloned using limiting dilution cloning. Candidate clones were screened for TNFR:Fc production as described above, and cell line designated A12 was selected. Subsequently, this cell line was adapted to growth in media without transferrin and IGF-1 by serial passaging in media without these two components. The final fully adapted cell line is referred to as VA12.

EXAMPLE 2

Culturing Conditions

A. 2A5-3 Cell Line

2A5-3 cells are cultured in suspension tissue culture spinner flasks in non-selective growth media. The non-selective growth media can comprise IMX2.2 media supplemented with 7.5% (v/v) bovine serum and 2.0 mM glutamine. IMX2.2 media is a custom media formulation based on Ham's F-12 and DMEM and was developed at Immunex for high density cultivation. The composition of IMX2.2 media is shown in Table 2 below.

TABLE 2

| COMPONENT | IMX 1.2 G/l | IMX 2.2 g/l | IMX 2.4 g/l |
|---|---|---|---|
| L-Alanine | 0.03115 | 0.03115 | 0.03115 |
| L-Arginine, HCl | 0.7805 | 0.7805 | 0.7805 |
| L-Asparagine, H$_2$O | 0.1 | 0.1 | 0.1 |
| L-Aspartic Acid | 0.04655 | 0.04655 | 0.04655 |
| Biotin | 0.000025 | 0.000025 | 0.000025 |
| Calcium Chloride, Anhydrous | 0.1166 | 0.1166 | 0.1166 |
| D-Calcium Pantothenate | 0.00368 | 0.00368 | 0.00368 |
| Choline Chloride | 0.05086 | 0.05086 | 0.05086 |
| Cupric Sulfate, 5•H$_2$O | 0.0000088 | 0.0000088 | 0.0000088 |
| Cyanocobalamin | 0.00467 | 0.00467 | 0.00467 |
| L-Cysteine, HCl, H$_2$O | 0.12292 | 0.12292 | 0.12292 |
| L-Cystine, 2•HCl | 0.03129 | 0.03129 | 0.03129 |
| Dextrose, Anhydrous | 6.5 | 4.5 | 4.5 |
| Ferric Nitrate, 9•H$_2$O | 0.00005 | 0.00005 | 0.00005 |
| Ferrous Sulfate, 7•H$_2$O | 0.002919 | 0.002919 | 0.002919 |
| Folic Acid | 0.00655 | 0.00655 | 0.00655 |
| L-Glutamic Acid | 0.05145 | 0.05145 | 0.05145 |
| Glycine | | 0.04125 | 0.04125 |
| HEPES, FA | 3.5745 | 3.5745 | 3.5745 |
| L-Histidine, HCl, H$_2$O | 0.09436 | 0.09436 | 0.09436 |
| Hypoxanthine, Na Salt | | 0.0167 | 0.0167 |
| i-Inositol | 0.0666 | 0.0666 | 0.0666 |
| L-Isoleucine | 0.06629 | 0.06629 | 0.06629 |
| L-Leucine | 0.09835 | 0.09835 | 0.09835 |
| Linoleic Acid | 0.000294 | 0.000294 | 0.000294 |
| DL-Alpha-Lipoic Acid | 0.000735 | 0.000735 | 0.000735 |
| L-Lysine, HCl | 0.20075 | 0.20075 | 0.20075 |
| Magnesium Chloride, Anhydrous | 0.2003 | 0.2003 | 0.2003 |
| Magnesium Sulfate, Anhydrous | 0.04884 | 0.04884 | 0.04884 |
| L-Methionine | 0.03068 | 0.03068 | 0.03068 |
| Niacinamide | 0.002131 | 0.002131 | 0.002131 |
| Phenol Red | 8.6 | 8.6 | |
| L-Phenylalanine | 0.05036 | 0.05036 | 0.05036 |
| Potassium Chloride | 0.9826 | 0.9826 | 0.9826 |
| L-Proline | 0.12075 | 0.12075 | 0.12075 |
| Putrescine, 2•HCl | 0.000564 | 0.000564 | 0.000564 |
| Pyridoxal, HCl | 0.002 | 0.002 | 0.002 |
| Pyridoxine, HCl | 0.000217 | 0.000217 | 0.000217 |
| Riboflavin | 0.000333 | 0.000333 | 0.000333 |
| L-Serine | 0.05775 | 0.05775 | 0.05775 |
| Sodium Chloride | 4.0 | 4.0 | 1.0 |
| Sodium Phosphate, Dibasic, Anhydrous | 0.07102 | 0.07102 | 0.07102 |
| Sodium Phosphate, Monobasic, H$_2$O | 0.0625 | 0.0625 | 0.0625 |
| Sodium Pyruvate | 0.385 | 0.385 | 0.385 |
| Thiamine, HCl | 0.00319 | 0.00319 | 0.00319 |
| L-Threonine | 0.08915 | 0.08915 | 0.08915 |
| Thymidine | | 0.002555 | 0.002555 |
| L-Tryptophan | 0.01514 | 0.01514 | 0.01514 |
| L-Tyrosine, 2Na, 2•H$_2$O | 0.7913 | 0.7913 | 0.7913 |
| L-Valine | 0.08795 | 0.08795 | 0.08795 |
| Zinc Sulfate, 7•H$_2$O | 0.003021 | 0.003021 | 0.003021 |
| Pluronic F-68 | 1.0 | 1.0 | 1.0 |

The suspension culture is subcultivated in spinner flasks every 3±1 days until transfer to bioreactors. The culture is then expanded by inoculation into a perfusion bioreactor. In order to enhance all mass, the culture is perfused or continuously fed with non-selective growth media while the equivalent volume of spent media is removed. This seed tank is perfused over the course of 5±1 days at 37° C. with non-selective media containing 7.5% (v/v) bovine serum in order to generate a high cell density for inoculation of the production bioreactor.

At the end of the perfusion stage, the culture undergoes a medium exchange using serum-free non-selective growth media in order to reduce the serum levels. After medium exchange, the culture is used to inoculate a production bioreactor. The production bioreactor is inoculate at approximately $2.0 \times 10^6$ cells/ml. The production media may be IMX2.4 media supplemented with 100 mg/l of Intralipids (Kabi Pharmacia Inc., Clayton, N.C.) and 25 µg/l of IGF-1. IMX2.4 media is a custom media formulation based on Ham's F-12 and DMEM and was developed at Immunex for high density recombinant protein expression. The composition of IMX2.4 media is shown in Table 2 above.

Following inoculation, sodium butyrate may be added at a concentration of 1.0 mM per $1.0 \times 10^6$ cells/ml. The production culture is operated for 10±1 days at 28-34° C. Nutrient feeds are introduced into the production culture on days 2, 4 and 6. These feeds include 25 µg/l of IGF-1 on days 2, 4 and 6; 1.0 µM hydrocortisone on days 2 and 4; and 1X Ham's nutrient mixture F-12 on day 4. The osmolality of production culture maybe 250-400 mOsm using a pH 7.2.

B. VA12 Cell Line

VA12 cells are cultivated in suspension in tissue culture spinner flasks in serum-free selective growth media. The serum-free selective growth media may comprise nucleoside-free IMX1.2 media supplemented with 1X trace elements, 0.5% (w/v) soy hydrolysate, 5.0 mg/l of Intralipids, 6.5 mM L-glutamine, 6.5 g/l glucose and 150 mM methotrexate. The trace elements and concentrations at 1X are shown in the Table 3 below. IMX1.2 media is a custom nucleoside-free media formulation based on Ham's F-12 and DMEM and was developed at Immunex for high density suspension cultivation under selective (DHFR) conditions. The composition of IMX1.2 media is shown in Table 2 above.

TABLE 3

| Trace Elements | g/l |
| --- | --- |
| Barium acetate | 0.00000255 |
| Germanium dioxide | 0.00000053 |
| Potassium iodide | 0.00000017 |
| Silver nitrate | 0.00000017 |
| Zirconyl chloride, 8•H$_2$O | 0.00000322 |
| Aluminum chloride, 6•H$_2$O | 0.00000217 |
| Aluminum metavanadate | 0.00000124 |
| Cadium chloride, 6•H$_2$O | $6.02 \times 10^{-7}$ |
| Chrominum chloride, 6•H$_2$O | $4.21 \times 10^{-7}$ |
| Colbalt chloride, 6•H$_2$O | 0.00000238 |
| Manganous sulfate, H$_2$O | 0.00000017 |
| Nickel sulfate, 6•H$_2$O | 0.00000013 |
| Potassium bromide | 0.00000012 |
| Rubidium chloride | 0.00000121 |
| Sodium fluoride | 0.00000042 |
| Stannous chloride, 2•H$_2$O | 0.00000012 |

VA12 cells are suspension culture in tissue culture spinner flasks containing serum-free selective growth medium.

The suspension culture is subcultivated in spinner flasks every 3±1 days until transfer to bioreactors. The culture is expanded by inoculation into a perfusion bioreactor.

The perfusion bioreactor is perfused over the course of 5±1 days at 37° C. with serum-free perfusion media. Serum-free perfusion media may be IMX6.0 media supplemented with 1X trace elements, 0.5% (w/v) soy hydrolysate and 5.0 mg/l of Intralipids. IMX6.0 media is a custom media formulation based on Ham's F-12 and DMEM and was developed at Immunex for high density suspension cultivation under serum-free conditions. The composition of IMX6.0 media is shown in Table 4 below.

TABLE 4

| COMPONENT | IMX 6.0 g/l | IMX 7.0 g/l |
| --- | --- | --- |
| L-Alanine | 0.03738 | 0.0623 |
| L-Arginine, HCl | 0.9366 | 1.561 |
| L-Asparagine, H$_2$O | 0.17 | 0.5 |
| L-Aspartic Acid | 0.05586 | 0.0931 |
| Biotin | 0.00003 | 0.00005 |
| D-Calcium Pantothenate | 0.004416 | 0.00736 |
| Choline Chloride | 0.061032 | 0.10172 |
| Cupric Sulfate, 5•H$_2$O | 0.00001216 | 0.0000192 |
| Cyanocobalamin | 0.005712 | 0.00952 |
| L-Cysteine, HCl, H$_2$O | 0.147504 | 0.49184 |
| L-Cystine, 2HCl | 0.052548 | 0.12458 |
| Dextrose, Anhydrous | 6.5 | 6.5 |
| Ferric Nitrate, 9•H$_2$O | 0.00005 | 0.00005 |
| Ferrous Sulfate, 7•H$_2$O | 0.002919 | 0.0.002919 |
| Folic Acid | 0.00786 | 0.0131 |
| L-Glutamic Acid | 0.06174 | 0.1029 |
| Glycine | 0.0495 | 0.0825 |
| HEPES, FA | 3.5745 | 3.5745 |
| L-Histidine, HCl, H$_2$O | 0.113232 | 0.18872 |
| Hypoxanthine, Na Salt | 0.02004 | 0.0334 |
| i-Inositol | 0.07992 | 0.1332 |
| L-Isoleucine | 0.079548 | 0.13258 |
| L-Leucine | 0.11802 | 0.1967 |
| Linoleic Acid | 0.0003528 | 0.000588 |
| DL-Alpha-Lipoic Acid | 0.000882 | 0.00147 |
| L-Lysine, HCl | 0.2409 | 0.4015 |
| Magnesium Chloride, Anhydrous | 0.24036 | 0.4006 |
| Magnesium Sulfate, Anhydrous | 0.058608 | 0.09768 |
| L-Methionine | 0.066816 | 0.15136 |
| Niacinamide | 0.0025572 | 0.004262 |
| L-Phenylalanine | 0.060432 | 0.10072 |
| Potassium Chloride | 1.17912 | 1.9652 |
| L-Proline | 0.1449 | 0.4815 |
| Putrescine, 2HCl | 0.0006768 | 0.001128 |
| Pyridoxal, HCl | 0.0024 | 0.004 |
| Pyridoxine, HCl | 0.0002604 | 0.000434 |
| Riboflavin | 0.0003996 | 0.000666 |
| L-Serine | 0.0943 | 0.1155 |
| Sodium Chloride | 1.0 | 1.0 |
| Sodium Phosphate, Dibasic, Anhydrous | 0.85224 | 0.14204 |
| Sodium Phosphate, Monobasic, H$_2$O | 0.075 | 0.125 |
| Sodium Pyruvate | 0.462 | 0.77 |
| Thiamine, HCl | 0.003828 | 0.00638 |
| L-Threonine | 0.10698 | 0.1783 |
| Thymidine | 0.003066 | 0.00511 |
| L-Tryptophan | 0.028168 | 0.07528 |
| L-Tyrosine, 2Na, 2•H$_2$O | 0.114956 | 0.31826 |
| L-Valine | 0.10554 | 0.1759 |
| Zinc Sulfate, 7•H$_2$O | 0.0044882 | 0.006905 |
| L-Glutamine | 0.95 | 1.0 |
| Ferric Citrate | 0.0011551 | 0.0011551 |
| Hydrocortisone | | 0.0003625 |
| Hydrocortisone | | 0.0003625 |
| Sodium Meta-Silicate, 9•H$_2$O | 0.00014 | 0.00014 |
| Sodium Selenite | 0.0000173 | 0.0000173 |
| Pluronic F-68 | 1.0 | 1.0 |
| TRACE ELEMENTS | | |
| Barium Acetate | 0.00000255 | 0.00000255 |
| Germanium Dioxide | 0.00000053 | 0.00000053 |
| Potassium Iodide | 0.00000017 | 0.00000017 |
| Silver Nitrate | 0.00000017 | 0.00000017 |
| Ziroconyl Chloride, 8•H$_2$O | 0.00000322 | 0.00000322 |
| Aluminum Chloride, 6•H$_2$O | 0.00000217 | 0.00000217 |
| Ammonium Metavanadate | 0.00000085 | 0.00000085 |
| Ammonium Molybdate, 4•H$_2$O | 0.00000124 | 0.00000124 |
| Cadmium Chloride, Anhydrous | 0.000000602 | 0.000000602 |
| Chromium Chloride, 6•H$_2$O | 0.000000421 | 0.000000421 |
| Cobalt Chloride, 6•H$_2$O | 0.00000238 | 0.00000238 |
| Manganous Sulfate, H$_2$O | 0.00000017 | 0.00000017 |
| Nickel Sulfate, 6•H$_2$O | 0.00000013 | 0.00000013 |
| Potassium Bromide | 0.00000012 | 0.00000012 |
| Rubidium Chloride | 0.00000121 | 0.00000121 |

TABLE 4-continued

| COMPONENT | IMX 6.0 g/l | IMX 7.0 g/l |
|---|---|---|
| Sodium Fluoride | 0.0000042 | 0.0000042 |
| Stannous Chloride, 2•H$_2$O | 0.00000012 | 0.00000012 |

This seed tank is perfused over the course of 5±1 days at 37° C. with serum-free non-selective media, i.e., IMX6.0 media, in order to generate a high cell density for inoculation of a production bioreactor. The perfusion culture is used to inoculate a production bioreactor at 4.0-5.0×10$^6$ cells/ml in serum-free production media. The serum-free production media may be IMX7.0 supplemented with 1X trace elements, 0.5% (w/v) soy hydrolysate, 5.0 mg/l of Intralipids and 1.0 μM hydrocortisone. IMX7.0 media is a custom media formulation based on Ham's F-12 and DMEM and was developed at Immunex for high density production under serum-free conditions. The composition of IMX7.0 media is shown in Table 4 above.

Following inoculation, sodium butyrate may be added at a concentration of 1.5 mM. The production culture is operated for 12±1 day at 28-34° C. Feeds are introduced into the production culture throughout the run. On day 2 and 4, the production culture is fed with 1.0 μM of hydrocortisone, 0.3 g/l asparagine, 0.3 g/l glutamine, 0.09 g/l methionine and 0.045 g/l tryptophan. The osmolality of production culture maybe 250-400 mOsm, using a pH of 7.0.

EXAMPLE 3

Characterization of Supernatants

Supernatant samples from both the 2A5-3 and VA12 cell lines in which the production culture was operated at 34° C. for 2A5-3 samples and 30° C. for VA12 samples were protein A purified using a 1.0 ml column of protein A Sepharose fast flow resin (Pharmacia) mounted on a Supelco vacuum apparatus and which had been equilibrated with 0.025 M Tris (pH 7.4) containing 0.15 M NaCl. Supernatant, which had been passed though a 0.45 μm filter, was loaded, and washed once with 0.025 M Tris (pH 7.4) containing 0.15 M NaCl, then washed once with 0.025 M Tris (pH 7.4) containing 0.5 M NaCl, and then washed once with 0.025 M Tris (pH 7.4) containing 0.15 M NaCl. TNFR:Fc was eluted using 0.05 M sodium acetate (pH 4.0) containing 0.1 M NaCl, and immediately neutralized with 0.5 M Tris (pH 8.0).

Figure 4:
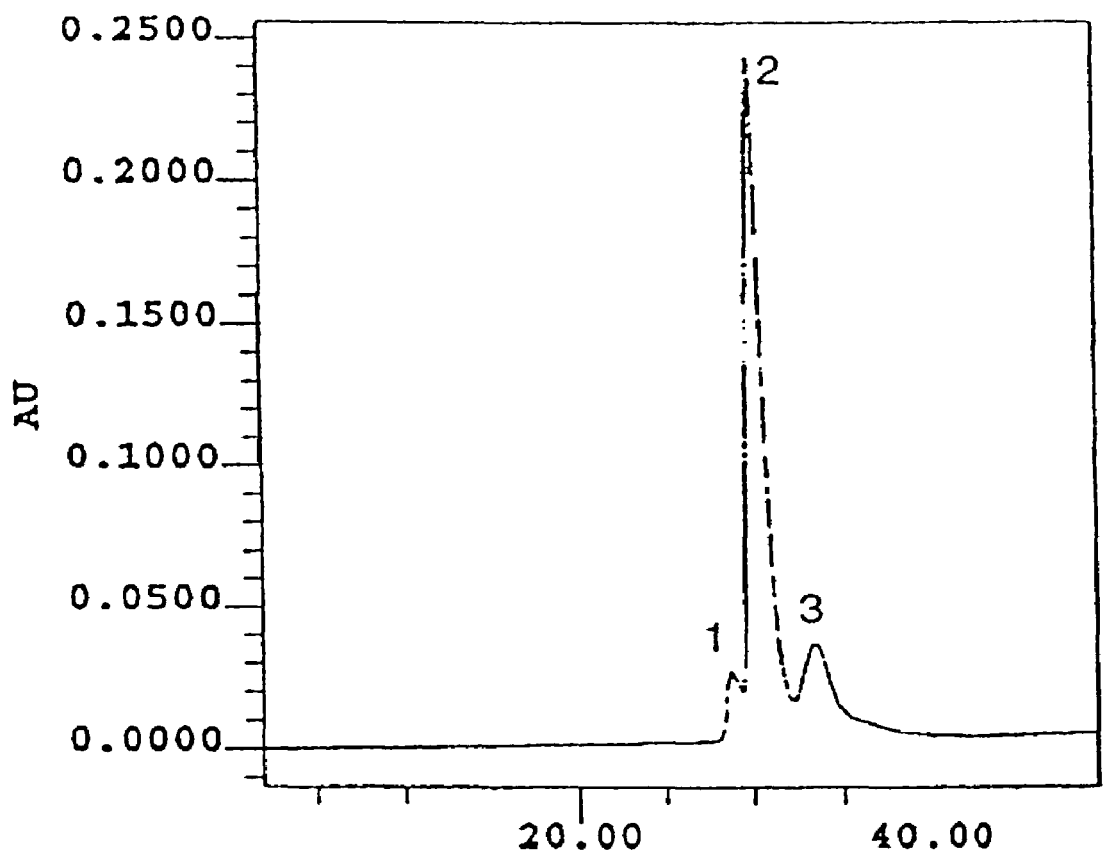
FIG. 4 shows a typical hydrophobic interaction chromatography HIC profile of recombinant CHO cell producing TNFR-II:Fc, and shows three peaks.

The resulting protein A purified supernatants were diluted to 2.0 mg/ml with water or PBS, and 20 μg were injected onto a TSK Butyl-NPR (0.46×3.5 cm) column. Elution was accomplished with a 50 min linear gradient between buffer comprising 1.8 to 0 M ammonium sulfate and 0.1 M sodium phosphate (pH 7.0) at a flow rate of 1.0 ml/min. A typical HIC profile, showing three peaks, is seen in FIG. 4.

A. Characterization of Peaks

SDS-PAGE of peak 3 on a Novex 8-16% gel showed that intact TNFR:Fc constitutes the large majority (estimated>80%) of total protein in this fraction with the remainder consisting predominantly of TNFR:Fc aggregates and fragments.

Peak 3 showed greatly reduced TNF-α binding activity (15%) compared to unfractionated material, whereas peak 2 showed enhanced TNF-α binding activity (118%) compared to unfractionated material.

In the binding activity assay, TNFR:Fc is captured by a solid-phase monoclonal antibody against the Fc region, followed by exposure to biotinylated TNF-α and avidin-horseradish peroxidase. The signal generated by the horseradish peroxidase is proportional to the binding activity of the TNFR:Fc. Activity is expressed in arbitrary units with the reference sample set to equal 100 units.

Peak 3 also showed greatly reduced bioactivity (11%) compared to unfractionated material, whereas again, peak 2 showed enhanced bioactivity (117%) compared to unfractionated material.

In the bioactivity assay, which was carried out as described by Nakai et al, *Biochem. Biophys. Res. Comm.*, 154:1189 (1988), A375 cells, derived from a human malignant melanoma, are killed in the presence of TNF-α. Soluble TNFR:Fc specifically neutralizes the inhibitory activity of TNF-α in a dose dependent manner. In practice, fixed amount of A375 cells and TNF-α are added to the wells of a microtiter plate along with a variable amount of TNFR:Fc. After a period of incubation, the live cells are quantitated which are directly proportional to the amount of neutralization of TNF-α by TNFR:Fc. Activity is expressed in terms of U/mg.

Similarly, when fractionation by HIC was carried out using a decreasing sodium acetate gradient instead of the ammonium sulfate gradient, peak 3 showed greatly reduced binding activity compared to peak 2 (<30 units vs. 162 units) and bioactivity (<0.34×10$^6$ U/mg. vs 2.71×10$^6$ U/mg), demonstrating that separation of TNFR:Fc into active and much less active fractions is not unique to the use of ammonium sulfate, i.e., the HIC results are not dependent on the use of a particular salt.

Very similar results, but with somewhat less resolution, were obtained when a Pharmacia Resource ISO column which contains an isopropanol ligand on a polystyrenedivinylbenzene backbone, was used in place of the TSK Butyl-NPR column, demonstrating that similar chromatographic profiles are obtained with different hydrophobic ligands and support matrices. That is, the activity of peak 3 is reduced independent of which HIC resin is used.

Next, the hypothesis was tested that an unknown factor present in peak 3 might be responsible for suppressing the binding and bioassay activities. To test this, equal volumes of peak 2 and peak 3 were mixed and diluted in two different ways:

(a) so that each component was present at its individual concentration, and (b) so that each component was present at ½ its individual concentration.

The results demonstrated that method "(a)" gives the sum of both individual activities and method "(b)" gives the average. Thus, there was no interference of peak 3 with the activity of peak 2.

Peak 3 contains some of the CHO proteins of the starting material. Thus, to test the hypothesis that these CHO proteins might interfere with activity measurements of this fraction, unfractionated CHO proteins were was spiked into peak 2 to a final concentration of 1.0% (10,000 ppm). This concentration was chosen because it is similar to the value (6500 ppm) quantitated in peak 3 by a CHO protein specific assay. The results demonstrated that spiking had no effect on binding or bioassay activities.

Next, purified TNFR:Fc was incubated for 3-7 hrs at 37° C. with either 1.0 mM L-cysteine or 0.4 mM DTT and analyzed by HIC. A broad newly formed HIC peak was observed that is extensively aggregated TNFR:Fc. Binding assays of the samples showed 129 Binding Units (n=3) prior to, and 56 Binding Units (n=3) after, DTT treatment. The percent activity decrease corresponds closely to the percentage of aggregates present, and suggests that only non-aggregated TNFR:Fc has significant activity.

Figure 5:
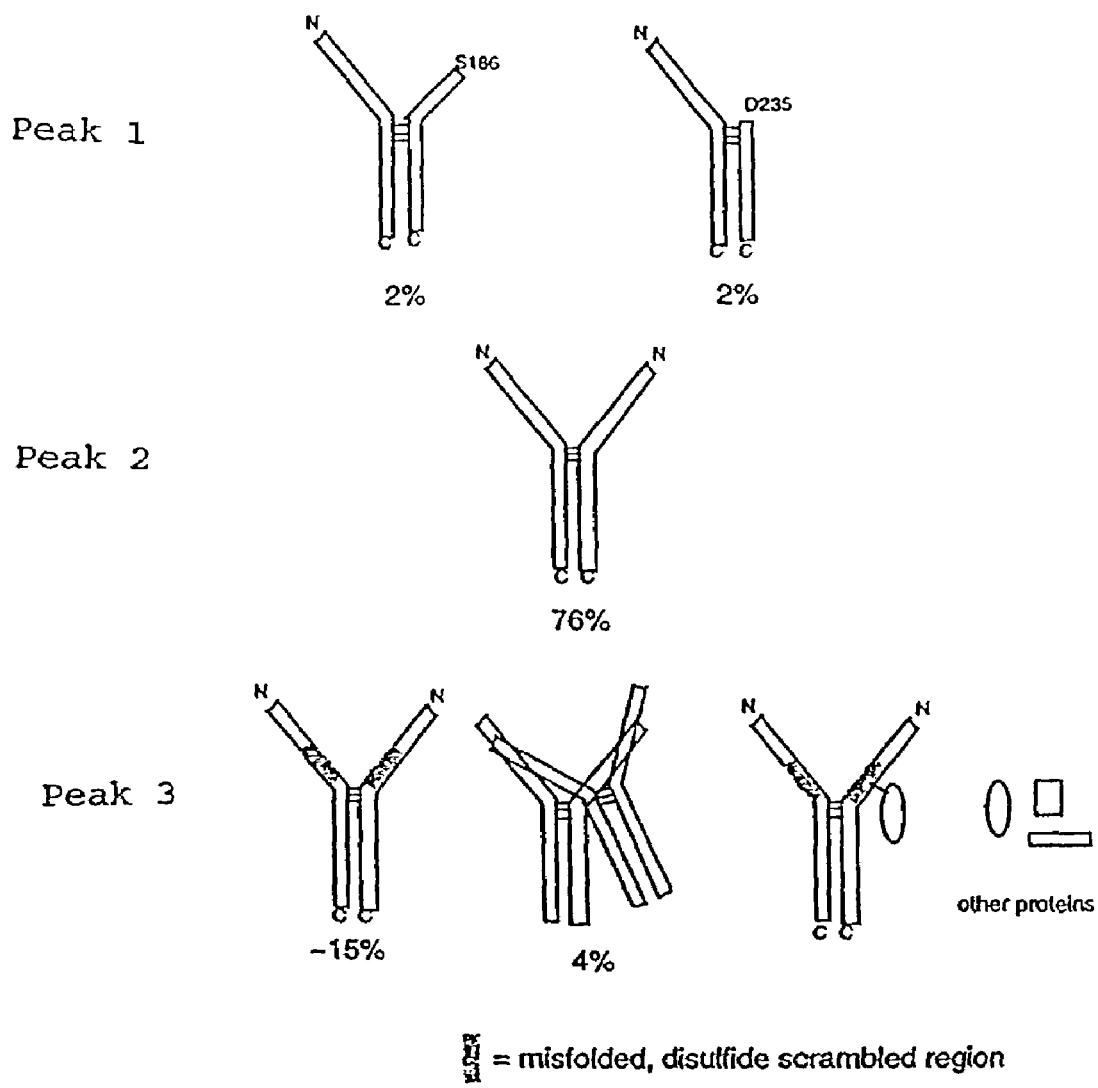
FIG. 5 summarizes the current knowledge of the compositions of peaks 1, 2 and 3 in the HIC profile of recombinant CHO cells producing TNFR-II:Fc.

By Edman sequencing, peak 1 was found to be "highly enriched" in S186 and D235 sequences. That is, it is believed that peak 1 consists of the hybrid dimer molecules which contain a full length TNFR:Fc chain paired with a truncated chain starting at either S186 or D235 (FIG. 5).

SDS-PAGE showed that peak 2 contains minimal aggregate levels on non-reducing gels and less low molecular weight (LMW) bands under both reducing and non-reducing conditions. Low levels of the S186 and D235 forms were detectable. Peak 3 showed both increased levels of aggregate, and enrichment of several LMW species unrelated to S186 and D235.

Edman sequencing was performed on bands excised from a PVDF blot of a Novex 14% gel. All except one of the Coomassie blue visible bands in peak 3 were found to be TNFR:Fc fragments.

Both peak 2 and peak 3 contain an isoelectric focusing (IEF) profile on a Novex (pH 3-10) gel similar to unfractionated TNFR:Fc. Following enzymatic desialytion however, peak 2 was noticeably more homogeneous and consisted predominantly of a single isoform of pI-8. Peak 3 consisted predominantly of several more acidic isoforms.

Anion-Exchange Chromatography (AEX) is more sensitive than IEF to subtle variations in charge. By this method, using a Pharmacia Mini-Q column at a flow rate of 0.8 ml/min and a linear gradient from 20 mM imidazole (pH 6.2) to 20 mM imidazole (pH 6.2), 0.7 M NaCl, peak 3 was found to be slightly more acidic, and peak 2 slightly more basic, than unfractionated TNFR:Fc. These trends are in agreement with the IEF results of desialylated samples.

Triplicate samples were assayed for sialic acid content with high performance anion-exchange chromatography using pulsed amphoteric detection (HPAEC-PAD) as described by Hardy et al, *Methods Enzymol.*, 230:208 (1994) following sialidase digestion. The results are shown in Table 5 below.

TABLE 5

| Sample | mol NANA/TNFR:Fc |
|---|---|
| Unfractionated | 12.3 ± 0.3 |
| Peak 2 | 12.0 ± 0.3 |
| Peak 3 | 12.2 ± 0.2 |

As shown in Table 5 above, no measurable differences between peaks 2 and 3 were observed.

Oligosaccharide profiles of peaks 2 and 3 were both highly similar to unfractionated TNFR:Fc samples. Quantitation of the peaks showed that all three samples are very similar. However, there was a small bias of increased percentage of O-linked oligosaccharides and decreased percentages of N-linked oligosaccharides in peak 3 vs. peak 2.

Next, matrix assisted laser desorption ionization time-of-flight mass spectroscopy (MALDI-TOF) was carried out on peaks 2 and 3 as described by Hillenkamp et al, *Anal. Chem.*, 63:1193A (1991). The spectra of peaks 2 and 3 showed two intense signals at 125 kDa and 63 kDa, the expected molecular and doubly charged ions of dimeric TNFR:Fc. Considering the heterogeneities present on the molecule, and the difficulty to exactly measure the peak centroid at this mass range, the experimental masses of the major species in peak 2 (124.98 kDa) and peak 3 (125.05 kDa) are identical. The spectrum of peak 2 appeared relatively clean with assignment of minor species. The spectrum of peak 3 exhibited a clear difference. At least five new ions at 17.1, 33.7, 46.4, 91.8 and 158.2 kDa were visible. The 17.1 and 33.7 kDa ions likely represent a single molecular species, as may the 46.4 and 91.8 kDa ions.

The MALDI-TOF spectra of reduced preparations of peaks 2 and 3 showed two major ions at 31 and 62 kDa that correspond to the singly and doubly charged ions of the expected TNFR:Fc monomer. However, three ions at 7.2, 14.7 and 29.2 kDa, absent from peak 2, were clearly visible on the peak 3 spectrum.

B. Summary of Characterization of Peaks

1. Peak 1

It is believed that peak 1 consists primarily of the S186 and D235 clipped molecules (FIG. 5).

2. Peak 2

This fraction is much more homogeneous than unfractionated material and consists of highly pure dimeric TNFR:Fc. It has ~18% higher specific activity in binding and bioactivity assays than unfractionated material (FIG. 5).

3. Peak 3

Visually, the shape of peak 3 often suggests that it is not homogeneous. Peak 3 can be further HIC-resolved into multiple peaks. In agreement with these observations, all characterization assays also indicated that peak 3 consists of multiple species.

The predominant species present in peak 3 is TNFR:Fc. Estimates from SDS-PAGE indicate that TNFR:Fc constitutes >80% of peak 3. No sialic acid or oligosaccharide profile differences are observed between peaks 2 and 3.

SDS-PAGE shows that peak 3 contains nearly all of the aggregated TNFR:Fc present initially.

Multiple LMW species are seen by SDS-PAGE (especially after reduction) and by MALDI-TOF (more prominent after reduction). Most of these have N-terminal sequences of TNFR:Fc fragments.

Direct results implying disulfide-scrambled TNFR:Fc in peak 3 come from incubating TNFR:Fc with catalytic amounts of reducing agents under non-denaturing conditions. The only effect on proteins should be to facilitate scrambling between solvent-exposed disulfides. This induced a broad, late-eluting HIC peak, which partially overlaps with peak 3 in samples with low protein concentrations, but elute later than peak 3 with conventional samples, e.g., at 53 mg/ml.

A plausible explanation, that unifies these observations, is that the TNFR:Fc in peak 3 contains localized, scrambled disulfides. This would almost certainly result in a more hydrophobic molecule (incorrect conformation) and increased HIC retention. To account for the 90% decrease in activity of peak 3, these scrambled disulfides should be located in the cysteine-rich TNFR domain so as to interfere with TNF-α binding. In addition, a lower percentage of TNFR:Fc molecules exhibit intermolecular disulfide scrambling with at least one, and possibly many more, CHO proteins. Addition of catalytic concentrations of thiols induces extensive disulfide scrambling which, at low protein concentrations, resembles (at least in part) peak 3, but at higher protein concentrations results in extensive aggregation (inter-molecular disulfide scrambling).

FIG. 5 summarizes the current knowledge of the compositions of peaks 1, 2 and 3.

EXAMPLE 4

Temperature Effects on 2A5-3 Cells

2A5-3 cells expressing TNFR:Fc were cultivated in bioreactors as described above except that cells were seeded at a density of $4.07 \times 10^6$ cells/ml, induction was carried out using 2.0 mM sodium butyrate, and the temperature of the production phase, which lasted 10 days, was varied. The culture supernatant was protein A purified and analyzed by HIC assay as described above. The results are shown in Table 6 below.

TABLE 6

| Temperature ° C. | HIC Peak 2% | HIC Peak 3% | Binding Mean Binding Units | Sialic Acid NANA (mol)/TNFR:Fc(mol) |
|---|---|---|---|---|
| 28 | 94 | 4 | 119 | 12 |
| 30 | 93 | 6 | 126 | 11 |
| 32 | 87 | 10 | 123 | 11 |
| 34 | 76 | 20 | 85 | 11 |
| 36 | 62 | 34 | 93 | 12 |
| 38 | 35 | 61 | 42 | 13 |

As shown in Table 6 above, lower process temperatures correlated with decreasing percentages of Peak 3, i.e., misfolded TNFR:Fc. Operation at 28° C. compared to 32° C. decreased TNFR:Fc productivity, but maximized Peak 2 yields. The results of binding and bioactivity assays shown in Table 6 above of samples with varying levels of peak 3 confirmed the inverse relationship between activity and percentage of peak 3. Maximum binding and bioactivity were observed with protein produced at 28° C.

EXAMPLE 5

Varying Conditions on VA12 Cell Line

A. Osmolality Study

VA12 cells were seeded at $2.0 \times 10^6$ cell/ml in duplicate shake flasks in serum-free production media. Medium osmolality was adjusted from 200 to 500 mOsM by varying NaCl concentration. Cultures were agitated at 150 rpm at 30° C. Day 7 supernatant samples were analyzed by HIC as described above. The results are shown in Table 7 below.

TABLE 7

| Osmolality mOsM | HIC Peak 2% | HIC Peak 3% |
|---|---|---|
| 250 | 50 | 50 |
| 300 | 46 | 54 |
| 350 | 46 | 54 |
| 400 | 51 | 49 |
| 450 | 54 | 46 |

Low product titer along with insufficient volume prevented analysis of the 200 and 500 mOsM cases. However, as shown in Table 7 above, HIC analysis of day 7 supernatant samples show no appreciable difference in yield of Peak 3.

B. Temperature, Transferrin, Butyrate and Peptone Study

Shake flasks were seeded with VA12 cells at $2.0 \times 10^6$ cell/ml (60 ml in a 250 ml flask) in production medium comprising 6.5 mg/l of glucose, IMX2.4 media, trace elements as shown in Table 3 above, 0.95 g/l L-glutamine, 0.15 g/l methionine, 1.0 µM of hydrocortisone, 150 µg/l of IGF-1 and 5.0 mg/l of Intralipids. The peptone tested was either N-Z Soy or Hy Soy (QUEST), transferrin was added at 10 mg/l or omitted, sodium butyrate was added at 1.0 mM or omitted and the production temperature was 30° or 34° C. Temperatures were monitored with certified incubator thermometers located on the shaker platform. Samples were taken on days 1, 3, 5 and 7 for cell counts and titer determination. At day 7, the supernatants were collected by centrifugation and filtered. Product was purified using 1.0 ml columns of protein A Sepharose fast flow resin mounted on a Supelco vacuum apparatus. The results are shown in Table 8 below.

TABLE 8

| Flask | Peptone | Temp ° C. | Transferrin mg/l | TNFR:Fc mg/l | Peak 2% | Peak 3% |
|---|---|---|---|---|---|---|
| 1 | N-Z | 30 | 10 | 129 | 78 | 21 |
| 2 | Hy | 30 | 10 | 130 | 77 | 22 |
| 3 | N-Z | 34 | 10 | 101 | 41 | 59 |
| 4 | Hy | 34 | 10 | 106 | 42 | 58 |
| 5 | N-Z | 30 | 0 | 162 | 80 | 20 |
| 6 | Hy | 30 | 0 | 117 | 79 | 20 |
| 7 | N-Z | 34 | 0 | 83* | 41* | 59* |
| 8 | Hy | 34 | 0 | 92 | 38 | 59 |

*average of duplicates

As shown in Table 8 above, peak 3 formation was not influenced by the absence and presence of bovine transferrin or the type of peptone. However, correlation with temperature was observed. The removal of bovine transferrin and substitution of N-Z Soy with Hy Soy resulted in an estimated 20 to 40% peak 3. An approximately three fold increase in HIC peak 3 was observed at 34° C. compared to 30° C.

Next, the effect of sodium butyrate on peak 3 formation was evaluated in a subset of flasks from this experiment. The results are shown in Table 9 below.

TABLE 9

| Flask | Butyrate mM | Temp ° C. | Transferrin mg/l | TNFR:Fc mg/l | Peak 2% | Peak 3% |
|---|---|---|---|---|---|---|
| 2A | 1 | 30 | 10 | 130 | 77 | 22 |
| 2B | 0 | 30 | 10 | 114 | 82 | 18 |
| 4A | 1 | 34 | 10 | 106 | 42 | 58 |
| 4B | 0 | 34 | 10 | 104 | 68 | 32 |
| 6A | 1 | 30 | 0 | 117 | 79 | 20 |
| 6B | 0 | 30 | 0 | 92 | 81 | 19 |
| 8A | 1 | 34 | 0 | 92 | 41 | 55 |
| 8B | 0 | 34 | 0 | 94 | 55 | 45 |

As shown in Table 9 above, while temperature again had the greatest effect on peak 3 formation, cultures grown at 34° C. with sodium butyrate produced more peak 3 compared to the cultures without inducer at that same temperature. However, difference in peak 3 production with and without sodium butyrate was minimal at 30° C.

C. Temperature and Growth Factor Study

Shake flasks were seeded with VA12 cells at $2.0 \times 10^6$ cell/ml (50 ml in a 250 ml flask) in T2 version 2 production medium. The sodium butyrate concentration was 1.0 mM. Hy Soy peptone was used for this study. The temperatures tested were 28°, 32°, 34° or 37° C. IGF-1 and recombinant insulin (Recombulin, full chain—Life Technologies) were tested at 150 µg/l. Product was purified using 1.0 ml columns of protein A Sepharose fast flow resin mounted on a Supelco vacuum apparatus. The results are shown in Table 10 below.

TABLE 10

| Temp °C. | Growth Factor | Viable Cell Density 10⁵ c/ml | Viability % | TNFR: Fc mg/l | Cum QP pg/cell/day | Peak 2% | Peak 3% |
|---|---|---|---|---|---|---|---|
| 28 | IGF-1 | 8.20 | 33 | 184 | 25.0 | 84 | 16 |
| 32 | IGF-1 | 20.17 | 73 | 212 | 17.5 | 58 | 43 |
| 34 | IGF-1 | 18.00 | 57 | 192 | 14.7 | 37 | 63 |
| 37 | IGF-1 | 16.83 | 46 | 48 | 2.7 | 19 | 81 |
| 28 | Insulin | 9.00 | 33 | 140 | 13.1 | 80 | 20 |
| 32 | Insulin | 14.67 | 49 | 261 | 22.7 | 56 | 44 |
| 34 | Insulin | 18.50 | 46 | 181 | 12.6 | 34 | 66 |
| 37 | Insulin | 8.17 | 26 | 45 | 4.7 | 16 | 84 |

As shown in Table 10 above, lower percentage of peak 3 correlates with lower temperature. The type of growth factor has no effect. Cell density and viability were higher in the 32° C. to 34° C. range. The level of peak 3 was independent of mitogen type, but correlated to operating temperature. Lower levels of misfolded TNFR:Fc correlated to lower temperatures, with a minimum of <20% observed at 28° C. Volumetric productivity of the IGF-1 case was maximal at 32° C.; however, peak 2 titer was highest at 28° C. Protein A purified material from the IGF-1 case was analyzed by binding and biological activity assays. The results are shown in Table 11 below.

TABLE 11

| Temp °C. | TNFR:Fc mg/l | Peak 2% | Peak 2 mg/l | Peak 3% | Binding Units (n = 2) | Bioassay 10⁶ units/mg (n = 2) |
|---|---|---|---|---|---|---|
| 28 | 184 | 84.4 | 155 | 15.6 | 92.7 | 2.07 |
| 32 | 212 | 57.5 | 122 | 42.5 | 77.0 | 1.62 |
| 34 | 192 | 37.4 | 72 | 62.6 | 48.8 | 0.95 |
| 37 | 48 | 19.3 | 9 | 80.7 | 18.3 | 0.49 |

As shown in Table 11 above, an inverse relationship between activity and percentage of peak 3 was observed. It is also important to note that protein from the 28° C. case also had the a highest binding and total TNF-neutralizing activity.

In summary, peak 3 levels were higher when cells were cultured in the presence of 1.0mM sodium butyrate at 34° C. However, no significant effects on peak 3 levels were observed due to the medium osmolality (250-450 mOsM, achieved by varying the NaCl concentration), the absence and presence of 10 mg/l of transferrin, the type of peptone (Hy Soy vs. N-Z Soy), or the type of mitogen (IGF-1 vs. recombinant insulin, 150 µg/l).

Temperature is typically lowered from 37° C. to 30-34° C. to increase titers of recombinant proteins and retroviral vectors. However, there is no mention in the prior art of its use to increase expression in favor of a product with specific characteristics or of specific quality. The temperature employed in the present invention actually decreases overall titer of TNFR:Fc, but significantly improves the quality thereof, by reducing peak 3.

While the invention has been described in detail, and with reference to specific embodiments thereof, it will be apparent to one of ordinary skill in the art that various changes and modifications can be made therein without departing from the spirit and scope thereof.

What is claimed is:

1. A method for recombinant production of TNFR:Fc comprising culturing a recombinant mammalian host cell which encodes and expresses TNFR:Fc so as to produce said TNFR:Fc, and obtaining the TNFR:Fc so produced, wherein during a production phase in serum-free medium, said host cell is cultured at a temperature of 25-34° C., wherein said TNFR:Fc comprises amino acids 1-163 of SEQ ID NO:12, wherein said method results in reduction in disulfide scrambling in the TNFR:Fc produced compared to when carrying out the production phase at a temperature of 37° C.

2. The method of claim 1, wherein said Fc is derived from an immunoglobulin molecule selected from the group consisting of IgG, IgM, IgA and IgE.

3. The method of claim 2, wherein said immunoglobulin molecule is IgG.

4. The method of claim 3, wherein said immunoglobulin molecule is $IgG_1$, or $IgG_3$.

5. The method of claim 1, wherein said TNFR:Fc comprises amino acids 1-185 of SEQ ID NO:12.

6. The method of claim 1, wherein said TNFR:Fc comprises amino acids 1-235 of SEQ ID NO:12.

7. The method of claim 1, wherein during the production phase, said host cell is cultured at a temperature of 25-30° C.

8. The method of claim 7, wherein during the production phase, said host cell is cultured at a temperature of 26-29° C.

9. The method of claim 8, wherein during the production phase, said host cell is cultured at a temperature of 27-28° C.

10. The method of claim 9, wherein during the production phase, said host cell is cultured at a temperature of 28° C.

11. The method of claim 1, wherein said production phase is carried out in the presence of an alkanoic acid or salt thereof.

12. The method of claim 11, wherein said alkanoic acid or salt thereof is selected from the group consisting of butyric acid, sodium butyrate or dibutyl cAMP.

13. The method of claim 12, wherein said alkanoic acid or salt thereof is sodium butyrate.

14. The method of claim 11, wherein said alkanoic acid is employed in a concentration of 0.1-5.0 mM.

15. The method of claim 14, wherein said alkanoic acid is employed in a concentration of 0.25-2.0 mM.

16. The method of claim 1, wherein said production phase is carried out at an osmolality of 200-400 mOsm.

17. The method of claim 16, wherein said osmolality is 240-350 mOsm.

18. The method of claim 1, wherein said production phase is carried out at a pH of about 6.6-7.4.

19. The method of claim 18, wherein said pH is about 6.8-7.0.

20. The method of claim 1, wherein said host cell is a CHO cell.

21. The method of claim 20, wherein said CHO cell is a dhfr- CHO cell.

22. The method of claim 1, wherein said production phase is preceded by a transition phase where the temperature is lowered from about 37° C. to about 28-34° C.

23. The method of claim 1, wherein said production phase is preceded by a transition phase where an alkanoic acid is added to the culture.

24. The method of claim 1, wherein said production phase is carried out as a batch or fed batch.

25. The method of claim 24, wherein said production phase is carried out in the presence of 0.1-5.0 mM of an alkanoic acid or salt thereof and an osmolality of 200-400 mOsm.

26. The method of claim 24, wherein said production phase is preceded by a transition phase where the temperature is lowered from about 37° C to about 28-34° C.

27. The method of claim 26, wherein said transition phase is cultured in serum-free medium.

28. The method of claim 1, wherein said production phase is preceded by a growth phase, wherein said growth phase is cultured in serum-free medium.

29. The method of claim 1, wherein said culturing is carried out in the absence of growth hormone.

30. A method for recombinant production of TNFR:Fc comprising culturing, in serum-free medium, recombinant dhfr CHO cells which encode and express TNFR:Fc so as to produce said TNFR:Fc, and obtaining the TNFR:Fc so produced, wherein TNFR:Fc comprises amino acids 1-235 of SEQ ID NO:12, wherein said Fc is derived from IgG$_1$, wherein during a production phase, said CHO cells are cultured at a temperature of 28-34° C in the presence of about 1.0 mM sodium butyrate/$10^6$ cells, at an osmolality of 250-400 mOsm, and a pH of about 7.2, wherein said method results in reduction in disulfide scrambling in the TNFR:Fc produced compared to when carrying out the production phase at a temperature of 37° C.

31. The method of claim 30, wherein said production phase occurs for 10±1 days.

32. A method for recombinant production of TNFR:Fc comprising culturing, in serum-free media, recombinant dhfr CHO cells which encode and express TNFR:Fc so as to produce said TNFR:Fc, and obtaining the TNFR:Fc so produced, wherein TNFR:Fc comprises amino acids 1-235 of SEQ ID NO:12, wherein said Fc is derived from IgG$_1$, wherein during a production phase, said CHO cells are cultured at a temperature of 28-34° C in the presence of about 1.5 mM sodium butyrate, at an osmolality of 250-400 mOsm, and a pH of about 7.0, wherein said method results in reduction in disulfide scrambling in the TNFR:Fc produced compared to when carrying out the production phase at a temperature of 37° C.

33. The method of claim 32, wherein said production phase occurs for 12±1 days.

* * * * *